(12) United States Patent
Gering et al.

(10) Patent No.: US 9,206,210 B2
(45) Date of Patent: Dec. 8, 2015

(54) IONIC LIQUIDS, ELECTROLYTE SOLUTIONS INCLUDING THE IONIC LIQUIDS, AND ENERGY STORAGE DEVICES INCLUDING THE IONIC LIQUIDS

(75) Inventors: Kevin L. Gering, Idaho Falls, ID (US); Mason K. Harrup, Idaho Falls, ID (US); Harry W. Rollins, Idaho Falls, ID (US)

(73) Assignee: BATTELLE ENERGY ALLIANCE, LLC, Idaho Falls, ID (US)

( * ) Notice: Subject to any disclaimer, the term of this patent is extended or adjusted under 35 U.S.C. 154(b) by 1060 days.

(21) Appl. No.: 13/253,707

(22) Filed: Oct. 5, 2011

(65) Prior Publication Data

US 2013/0089793 A1 Apr. 11, 2013

(51) Int. Cl.
| | |
|---|---|
| *C07F 9/6593* | (2006.01) |
| *H01M 10/052* | (2010.01) |
| *H01M 10/0567* | (2010.01) |
| *H01M 10/0569* | (2010.01) |

(52) U.S. Cl.
CPC ......... *C07F 9/65815* (2013.01); *H01M 10/052* (2013.01); *H01M 10/0567* (2013.01); *H01M 10/0569* (2013.01); *H01M 2220/20* (2013.01); *H01M 2300/0028* (2013.01); *H01M 2300/0037* (2013.01); *H01M 2300/0045* (2013.01); *Y02E 60/122* (2013.01)

(58) Field of Classification Search
CPC ............ C07F 9/65815; H01M 10/052; H01M 10/0567; H01M 10/0569; H01M 2220/20; H01M 2300/0028; H01M 2300/0037; H01M 2300/0045; Y02E 60/122
USPC ................................ 429/336; 546/22; 564/16
See application file for complete search history.

(56) References Cited

U.S. PATENT DOCUMENTS

| | | | |
|---|---|---|---|
| 6,469,224 B1 | 10/2002 | Nobori et al. | |
| 7,347,954 B2 | 3/2008 | Banno et al. | |
| 7,471,502 B2 | 12/2008 | Sato et al. | |
| 7,479,353 B2 | 1/2009 | Hollenkamp et al. | |
| 7,582,380 B1 | 9/2009 | Dunstan et al. | |
| 7,718,826 B2 | 5/2010 | Otsuki et al. | |
| 7,824,800 B1 | 11/2010 | Dunstan et al. | |

(Continued)

FOREIGN PATENT DOCUMENTS

| | | | |
|---|---|---|---|
| EP | 1970990 | * | 9/2008 |
| JP | 2001052736 A | | 2/2001 |

(Continued)

OTHER PUBLICATIONS

Rapko, "The Reactions of Trimethyloxonium Fluoroborate with Akylamino- and Phenyl-Substituted Cyclotriphosphonitriles" Inorganic Chemistry, 1970. 9, 1401-1405.*

(Continued)

*Primary Examiner* — Jafar Parsa
*Assistant Examiner* — Amy C Bonaparte
(74) *Attorney, Agent, or Firm* — TraskBritt

(57) ABSTRACT

An ionic liquid including a phosphazene compound that has a plurality of phosphorus-nitrogen units and at least one pendant group bonded to each phosphorus atom of the plurality of phosphorus-nitrogen units. One pendant group of the at least one pendant group comprises a positively charged pendant group. Additional embodiments of ionic liquids are disclosed, as are electrolyte solutions and energy storage devices including the embodiments of the ionic liquid.

16 Claims, 11 Drawing Sheets

(56) References Cited

U.S. PATENT DOCUMENTS

| | | | |
|---|---|---|---|
| 7,833,677 | B2 | 11/2010 | Kishi et al. |
| 7,951,495 | B2 | 5/2011 | Otsuki et al. |
| 2004/0256743 | A1 | 12/2004 | Funaki et al. |
| 2005/0255385 | A1 | 11/2005 | Harrup et al. |
| 2010/0209783 | A1 | 8/2010 | Siret et al. |
| 2010/0304223 | A1 | 12/2010 | Otsuki et al. |
| 2011/0177428 | A1 | 7/2011 | Dai et al. |
| 2011/0236765 | A1 | 9/2011 | Matsui et al. |

FOREIGN PATENT DOCUMENTS

| | | |
|---|---|---|
| JP | 2001338682 A | 12/2001 |
| JP | 2006036709 A | 2/2006 |
| JP | 2010-270077 A | 12/2010 |
| KR | 20080113968 A | 12/2008 |

OTHER PUBLICATIONS

Oakley, "The deprotonation and rearrangment of N-methyl methylphosphazenium quaternary salts: a novel synthetic route to cyclic azaphosphorins" Can. J. Chem., 1977, 55, p. 3651-3663.*

Schmidpeter, "Phosphazene. XLVI: P-Hydrogen-cyclotriphosphazene" Z. anorg. Allg. Chem., 394, p. 171-186, 1972.*

Zhang, "Phosphazene Cations" Inorganic Chemistry, 2006, 45, p. 10446-10448.*

Allcock "Quaternized Cyclic and High Polymeric Phosphazenes and Their Interactions with Tetracyanoquinodimethane" Inorganic Chemistry, 1986, 25, 2281-2288.*

Full English Translation of Schmidpeter ("Phosphazene. XLVI: P-Hydrogen-cyclotriphosphazene" Z. anorg. Allg. Chem., 394, 171-186, 1972), 31 pages.*

Allcock et al. ("Alkanesulfonation of Cyclic and High Polymeric Phosphazenes" Macromolecules 1993, 26,p. 5512-2219).*

Montoneri et al. ("Complexes of Hexaphenoxycyclotriphosphazene and Sulfur Trioxide" Inorganic Chemistry, 1991, 30, p. 150-152).*

Omotowa et al., "Phosphazene Based Ionic Liquids: Synthesis, Temperature Dependent Viscosity, and Effect as Additives in Water Lubrication of Silicon Nitride Ceramics," Inorg. Chem. 43:5466 5471 (2004).

PCT International Search Report and Written Opinion of the International Searching Authority for PCT/US2012/056838, dated Dec. 11, 2012, 11 pages.

Schwesinger et al. "Anhydrous Phosphazenium Fluorides and Sources for Extremely Reactive Fluoride Ions in Solution", Chemistry—A European Journal, vol. 12, No. 2, dated Sep. 30, 2005, pp. 438-445.

Allcock et al., "Synthesis and Hydrolysis of Hexakis(imidazolyl)cyclotriphosphazene," J. Am. Chem. Soc., 1981, 103, pp. 2250-2256.

Office Action and Search Report for Chinese Patent Application No. 201280048753.9, Dated Jun. 15, 2015, 31 pages.

* cited by examiner

US 9,206,210 B2

IONIC LIQUIDS, ELECTROLYTE SOLUTIONS INCLUDING THE IONIC LIQUIDS, AND ENERGY STORAGE DEVICES INCLUDING THE IONIC LIQUIDS

STATEMENT REGARDING FEDERALLY SPONSORED RESEARCH OR DEVELOPMENT

This invention was made with government support under Contract Number DE-AC07-05ID14517 awarded by the United States Department of Energy. The government has certain rights in the invention.

TECHNICAL FIELD

The disclosure, in various embodiments, relates generally to ionic liquids. More specifically, the disclosure, in various embodiments, relates to phosphazene-based ionic liquids, electrolyte solutions including the ionic liquids, and energy storage devices that utilize the ionic liquids.

BACKGROUND

An ionic liquid is a salt in a liquid state. Ionic liquids are also commonly known as liquid electrolytes, ionic melts, ionic fluids, fused salts, liquid salts, or ionic glasses. Ionic liquids are used as solvents or electrolytes due to their desirable properties, such as absence of a vapor pressure, high heat resistance and broad liquid temperature range, non-flammability, chemical stability, high ionic conductivity, high decomposition, and handleability in air.

As described in "Phosphazene-Based Ionic Liquids: Synthesis, Temperature-Dependent Viscosity, and Effect as Additives in Water Lubrication of Silicon Nitride Ceramics," Omotowa et al., *Inorg. Chem.* 43:5466-5471 (2004), phosphazene-based ionic liquids have been investigated for use as lubricants for aircraft gas turbine engines and as additives in water lubrication of silicon nitride ceramics.

Phosphazene-based ionic liquids have also been proposed for use in electrolyte solutions. U.S. Pat. Nos. 7,718,826 and 7,951,495 describe phosphazene-based ionic liquids where one or more quaternized nitrogen atoms are directly bonded to phosphorus atoms of the phosphazene compound. Thus, the ionic liquids include a charge localized at the quaternized nitrogen atom. The specific examples of phosphazene-based ionic liquids include direct phosphorus-fluorine bonds, which are labile and unstable under cell voltage conditions. The free fluoride released is an aggressive reactant and detrimental to cell performance.

Electrolyte solutions used in lithium-ion batteries are typically unstable at high temperatures and high voltages. Over time, the electrolyte solution turns into a tar-like material at high temperatures, which has precluded rapid deployment of lithium-ion batteries in vehicular applications, such as in hybrid electric vehicles (HEVs) and plug-in type hybrid electric vehicles (PHEVs). Improved electrolyte solutions are needed to advance the usefulness of lithium-ion batteries.

BRIEF SUMMARY

An embodiment of the disclosure includes an ionic liquid comprising a phosphazene compound comprising a plurality of phosphorus-nitrogen units and at least one pendant group bonded to each phosphorus atom of the plurality of phosphorus-nitrogen units. One pendant group of the at least one pendant group comprises a positively charged pendant group.

Another embodiment of the disclosure includes an ionic liquid comprising a phosphazene compound comprising a plurality of phosphorus-nitrogen units and at least one pendant group bonded to each phosphorus atom of the plurality of phosphorus-nitrogen units. A nitrogen atom of one of the phosphorus-nitrogen units is positively charged.

Yet another embodiment of the disclosure includes an ionic liquid comprising a phosphazene compound comprising a plurality of phosphorus-nitrogen units and at least one pendant group bonded to each phosphorus atom of the plurality of phosphorus-nitrogen units. A phosphorus atom of one of the phosphorus-nitrogen units is positively charged.

Yet still another embodiment of the disclosure includes an electrolyte solution comprising a solvent and an ionic phosphazene compound. The ionic phosphazene compound comprises a plurality of phosphorus-nitrogen units with a positively charged pendant group bonded to at least one of the phosphorus atoms of the phosphorus-nitrogen units, a positively charged nitrogen atom on one of the phosphorus-nitrogen units, or a positively charged phosphorus atom on one of the phosphorus-nitrogen units.

Another embodiment of the disclosure includes an energy storage device comprising a positive electrode, a negative electrode, a separator between the positive electrode and the negative electrode, and an electrolyte solution. The electrolyte solution is as previously described.

DETAILED DESCRIPTION

Phosphazene ionic liquids are disclosed, as are electrolyte solutions and energy storage devices including the phosphazene ionic liquids. As used herein, the term "phosphazene ionic liquid" means and includes a phosphazene compound that is a liquid at a temperature range at which the phosphazene ionic liquid is to be used and includes a cationic portion associated with or bonded to an anionic portion. The phosphazene compound has an overall neutral charge and is an ionic compound that includes the cationic portion and the anionic portion. The cationic portion of the phosphazene ionic liquid includes a plurality of phosphorus-nitrogen units with at least one pendant group bonded to each phosphorus atom of the phosphorus-nitrogen units, and the anionic portion includes an anionic group. At least one pendant group may also be bonded to a nitrogen atom of the phosphorus-nitrogen units. The phosphazene ionic liquid may be used in an electrolyte solution, which, in turn, is used in an energy storage device. The energy storage device may be a device that chemically, physically, or physicochemically stores electricity.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof. As used herein, the term "may" with respect to a material, structure, feature or method act indicates that such is contemplated for use in implementation of an embodiment of the disclosure and such term is used in preference to the more restrictive term "is" so as to avoid any implication that other, compatible materials, structures, features and methods usable in combination therewith should or must be, excluded.

Figure 1:
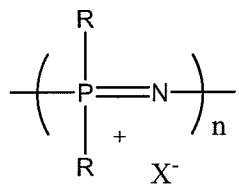
FIG. 1 is a general chemical structure of a phosphazene ionic liquid according to an embodiment of the disclosure.

The phosphazene ionic liquid includes a plurality of phosphorus-nitrogen units with at least one pendant group bonded to the phosphorus atoms of the phosphorus-nitrogen units. The phosphazene ionic liquid has the general chemical structure shown in FIG. 1, where n is from 3 to 8, each R is the pendant group, and "X$^-$" is the anionic portion of the phosphazene ionic liquid. The cationic portion of the phosphazene ionic liquid is indicated in FIG. 1 by the "+" symbol. Each of the pendant groups on each of the phosphorus atoms may be the same as or different from one another. The pendant groups are as described below. While not shown in FIG. 1, a pendant group(s) may also be bonded to a nitrogen atom(s) of the phosphorus-nitrogen units. While various embodiments herein describe or illustrate the phosphazene ionic liquid as a six-membered cyclic compound, i.e., n=3, the phosphazene ionic liquid may include from a six-membered to a sixteen-membered cyclic compound or may be an acyclic (e.g., linear) compound. Each phosphorus-nitrogen unit includes a double bond between the phosphorus atom and the nitrogen atom, and each phosphorus-nitrogen unit is bonded to an adjacent phosphorus-nitrogen unit through a single bond. The phosphazene ionic liquid may be cyclic or acyclic (e.g., linear).

The pendant groups on the phosphazene ionic liquid may be selected based on desired properties of the phosphazene ionic liquid. In addition to being a liquid at room temperature and at the temperature of use, the phosphazene ionic liquid may exhibit a low viscosity, a high lithium salt dissolution, stability at high voltage (greater than approximately 4.5 V), low flammability, and low volatility. The melting point of the phosphazene ionic liquid may be in a range of from approximately −30° C. to approximately 10° C. so that the phosphazene ionic liquid is a liquid at the temperature of use. However, the phosphazene ionic liquid may be used in an energy storage device, such as a battery, that operates at a temperature of from approximately −25° C. to approximately 150° C. The viscosity of the phosphazene ionic liquid at 20° C. may be similar to that of water (approximately 1.002 N s/m$^2$ (Pa s) at 20° C.), such as less than or equal to approximately 1000 centipoise (cP) at 20° C., such as from approximately 50 cP at 20° C. to approximately 500 cP at 20° C. In one embodiment, the viscosity of the phosphazene ionic liquid is from approximately 100 cP at 20° C. to approximately 200 cP at 20° C. By appropriately selecting the pendant groups, the viscosity and stability of the phosphazene ionic liquid may be tailored. The viscosity of the phosphazene ionic liquid may be directly proportional to the molecular weight of the phosphazene ionic liquid, which is, in turn, affected by the molecular weight of the pendant groups. By minimizing the molecular weight of the pendant groups and, thus, the molecular weight of the phosphazene ionic liquid, the phosphazene ionic liquid may exhibit a viscosity within the desired range. In addition, the pendant groups may be selected such that the phosphazene ionic liquid has an effective lithium salt dissolution of at least 1.0 molar concentration at room temperature (from approximately 20° C. to approximately 27° C.). If, however, the phosphazene ionic liquid is to be used as an additive of the electrolyte solution, the lithium salt dissolution and viscosity of the phosphazene ionic liquid may be lesser and greater, respectively, than the above-mentioned ranges accounting for mixture effects with the electrolyte solution.

Figure 2A:
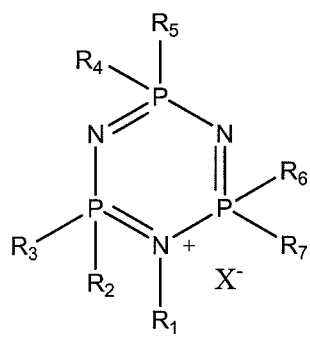
FIGS. 2A-2D are general chemical structures of phosphazene ionic liquids according to embodiments of the disclosure.
Figure 2B:
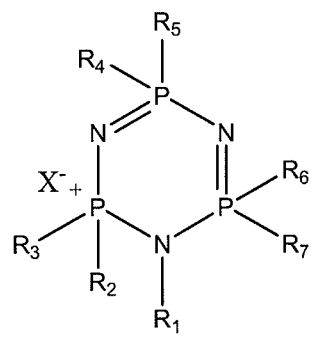
Figure 2C:
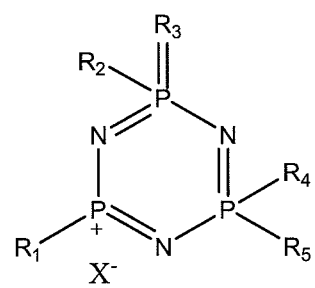
Figure 2D:
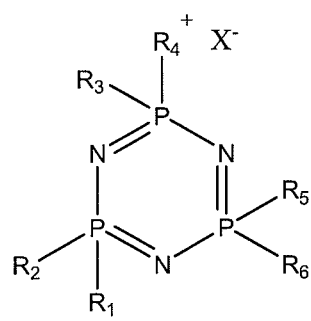

The locus of positive charge of the phosphazene ionic liquid may be a cationic pendant group(s) bonded to the phosphorus atom(s) of the phosphazene ionic liquid, or the positive charge may be located on one of the phosphorus atom(s) or one of the nitrogen atom(s) of the phosphorus-nitrogen units. The location of the positive charge may affect the stability, viscosity, and other properties of the phosphazene ionic liquid. The phosphazene ionic liquid may have one of the chemical structures shown in FIG. 2A-2D, in which the positive charge is on one nitrogen atom of the phosphazene ring (FIG. 2A), one phosphorus atom of the phosphazene ring (FIG. 2B or 2C), or a terminal portion of a pendant group bonded to a phosphorus atom of the phosphazene ring (FIG. 2D). While the phosphazene ionic liquid shown in FIG. 2B does not include three double bonds between the phosphorus atoms and the nitrogen atoms of the phosphazene ring, the phosphazene ionic liquid is referred to herein as having three phosphorus-nitrogen units. The anionic portion of the phosphazene ionic liquid in indicated by "X$^-$" in FIGS. 2A-2D while the locus of positive charge is indicated by the "+" symbol. In one embodiment, the positive charge of the phosphazene ionic liquid is on the terminal portion of the pendant group, as shown in FIG. 2D. While FIGS. 2A-2D show cyclic phosphazene compounds, the phosphazene ionic liquid may be an acyclic (e.g., linear) phosphazene compound having a positive charge on the phosphorus atom or nitrogen atom of the phosphorus-nitrogen unit, or on a terminal portion of at least one of the pendant groups. Furthermore, while FIGS. 2A-2D show a single locus of positive charge on the phosphazene ionic liquid, multiple charged locations may be present as long as the desired viscosity and stability of the phosphazene ionic liquid is achieved. In one embodiment, the phosphazene ionic liquid includes three phosphorus-nitrogen units (n=3), as shown in FIGS. 2A-2D. In another embodiment, the phosphazene ionic liquid is cyclic, as shown in FIGS. 2A-2D. The phosphazene ionic liquid may have one of the general chemical structures shown in FIGS. 2A-2D, where $R_1$-$R_7$ and X$^-$ are as described below.

The pendant groups may be independently selected from hydrogen, an acyl group, an acylamino group, an acyloxy group, an alkyl group, an alkenyl group, an alkynyl group, an alkoxy group, an amino group, an alkylamino group, an alkylarylamino group, a dialkylamino group, an alkylthio group, an alkarylthio group, an aryl group, an arylamino group, a diarylamino group, an aryloxy group, an aralkyl group, an alkaryl group, an aralkoxy group, an alkaryloxy group, an arylthio group, an arylthio acyl group, an amino acid group, a carbamoyl group, a carbonamido group, a carboxyl group, a cyano group, a formyl group, a glycol group, a heteroalkyl group, a heteroaralkyl group, a heteroaryl group, a hydroxyl group, a nitro group, an oxy(aliphatic) group, an oxy(aliphatic)hydroxyl group, an oxy(alkyl)hydroxyl group, an oxycarbonyl group, an oxysulfonyl group, a perfluoroalkyl group, a phosphate group, a saccharide group, a sulfamoyl group, a sulfonamido group, a sulfonylamino group, a sulfonyl group, a sulfoxide group, a thio group, a thioalkaryl group, a thioaralkyl group, a trifluoroalkyl group, or an ureido group. Any of the above-mentioned groups may be further substituted with at least one substituent, such as with a halogen, sulfonyl, or phosphate moiety. However, to improve the stability of the phosphazene ionic liquid at high temperature and high cell voltage, the phosphazene ionic liquid may not include a halogen atom directly bonded to a phosphorus atom of the phosphorus-nitrogen unit. Thus, the phosphazene ionic liquid may not include direct phosphorus-halogen bonds, improving the stability of the phosphazene ionic liquid at high temperature and high cell voltage compared to conventional phosphazene ionic liquids.

The term "acyl" means and includes a group derived by the removal of one or more hydroxyl groups from a carboxylic acid. The acyl group may include, but is not limited to, a formyl group, an acetyl group, a propionyl group, a butylyl group, a benzoyl group, an isobutylyl group, or a valeryl group.

The term "alkyl" means and includes a saturated, straight, branched, or cyclic hydrocarbon containing from 1 carbon atom to 6 carbon atoms. Examples include, but are not limited to, methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The terms "alkenyl" and "alkynyl" mean and include a straight, branched, or cyclic hydrocarbon containing from 2 carbon atoms to 6 carbon atoms with at least one double or at least one triple bond, respectively.

The term "alkoxy" means and includes an alkyl group linked to an oxygen atom. The alkoxy group may include, but is not limited to, a methoxy group, an ethoxy group, a propoxy group, a butoxy group, a pentoxy group, a hexoxy group, or an alkoxy-substituted alkoxy group, such as a methoxy ethoxy group or a methoxy ethoxy ethoxy group.

The terms "alkylamino" or "dialkylamino" mean and include an amino group having one or two alkyl substituents, respectively.

The term "alkylarylamino" means and includes an alkyl group with an aryl substituent and an amino substituent.

The term "alkylthio" means and includes an alkyl group with a thio substituent.

The term "alkarylthio" means and includes an alkyl group and an aryl group linked to a sulfur atom.

The term "aryl" means and includes a phenyl group, a tolyl group, or a naphthyl group or a substituted phenyl group, a substituted tolyl group, or a substituted naphthyl group, wherein the substituent is a halo, alkyl, alkoxy, alkylthio, amide, amino, alkylamino, dialkylamino, haloalkyl, hydroxyalkyl, alkoxyalkyl, methylenedioxy, cyano, C(O) (lower alkyl), —$CO_2H$, —$SO_3H$, or —$CO_2$, and wherein the aryl group can have up to four substituents.

The terms "arylamino" and "diarylamino" mean and include an amino group having one or two aryl substituents, respectively.

The term "aryloxy" means and includes an aryl group linked to an oxygen atom. The aryloxy group may include, but is not limited to, a phenoxy group, a methylphenoxy group, or a methoxy phenoxy group.

The term "aralkyl" means and includes an aryl group with an alkyl substituent.

The term "alkaryl" means and includes an alkyl group with an aryl substituent. Examples include, but are not limited to, benzyl, substituted benzyl, phenethyl, or substituted phenethyl, wherein the substituents are as defined above for aryl groups.

The term "alkaryloxy" means and includes an alkyl group and an aryl group linked to an oxygen atom.

The term "aralkoxy" means and includes an aryl group and an alkyl group linked to an oxygen atom.

The term "arylthio acyl" means and includes an aryl group with a thio substituent and an acyl substituent.

The term "acylamino" means and includes an acyl group with an amino substituent.

The term "acyloxy" means and includes an acyl group bonded to an oxygen atom.

The term "glycol" means and includes a hydrocarbon containing two hydroxyl groups.

The term "halogen" means and includes fluoro, chloro, bromo, or iodo.

The term "heteroalkyl" means and includes an alkyl group that includes a heteroatom such as oxygen, sulfur, or nitrogen (with valence completed by hydrogen or oxygen) in the carbon chain or terminating the carbon chain.

The term "heteroaralkyl" means and includes an aromatic moiety that includes at least one sulfur atom, oxygen atom, or nitrogen atom in the aromatic ring.

The term "heteroaryl" means and includes an aromatic moiety that includes at least one sulfur atom, at least one oxygen atom, or at least one nitrogen atom in the aromatic ring, and that can be optionally substituted as described above for aryl groups. Examples include, but are not limited to, furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbozolyl, oxazolyl, thiazolyl, isothiazolyl, 1,2,4-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl.

The term "oxy(aliphatic)" means and includes an oxygen atom linked to an aliphatic group. The term "aliphatic" means and includes a non-aromatic compound formed of hydrogen and carbon and collectively refers to an alkyl, alkenyl, or alkynyl group.

The term "oxy(aliphatic)hydroxyl" means and includes an oxygen atom linked to an aliphatic group and a hydroxyl group.

The term "oxy(alkyl)hydroxyl" means and includes an oxygen atom linked to an alkyl group and a hydroxyl group.

The term "oxycarbonyl" means and includes an oxygen atom linked to a carbonyl group.

The term "oxysulfonyl" means and includes an oxygen atom linked to a sulfonyl group.

The term "perfluoroalkyl" means and includes an alkyl group in which each of the hydrogen atoms is substituted with fluorine.

The saccharide is a monosaccharide or a disaccharide. The term "monosaccharide" means and includes a sugar, such as glucose, fructose, galactose, xylose, ribose, arabinose, lyxose, ribulose, xylulose, or mannose. The term "disaccharide" means and includes a sugar containing two monosaccharides. The disaccharide may, for example, be sucrose, lactose, or maltose.

The term "sulfonamido" means and includes a sulfonyl group bonded to an amido group.

The term "sulfonylamino" means and includes a sulfonyl group bonded to an amino group.

The term "sulfoxide" means and includes a compound in which a sulfur and oxygen atom are bonded to one another and 2 carbon atoms are bonded to the sulfur atom.

The term "thioaralkyl" means and includes an aryl group and an alkyl group linked to a sulfur atom.

The term "trifluoroalkyl" means and includes an alkyl group with a trifluoro substituent.

Any of the above-mentioned groups may be further substituted with at least one substituent, such as with a halogen, sulfonyl, or phosphate moiety.

In embodiments of the disclosure in which the ionic charge is present on the nitrogen atom (see FIG. 2A) or the phosphorus atom (see FIG. 2B or 2C) of the phosphorus-nitrogen unit, the pendant group may be bonded to the nitrogen atom or phosphorus atom by way of a carbon atom, an oxygen atom, a nitrogen atom, or a sulfur atom. Using oxygen or sulfur as the atom through which the pendant group is bonded to the nitrogen atom or phosphorus atom may enhance lithium solubility by improved solvent polarity and permittivity. Each of the pendant groups may be hydrogen, an acyl group, an acylamino group, an acyloxy group, an alkyl group, an alkenyl group, an alkynyl group, an alkoxy group, an amino group, an alkylamino group, an alkylarylamino group, a dialkylamino group, an alkylthio group, an alkarylthio group, an aryl group, an arylamino group, a diarylamino group, an aryloxy group, an aralkyl group, an alkaryl group, an aralkoxy group, an alkaryloxy group, an arylthio group, an arylthio acyl group, an amino acid group, a carbamoyl group, a carbonamido group, a carboxyl group, a cyano group, a formyl group, a glycol group, a heteroalkyl group, a heteroaralkyl group, a heteroaryl group, a hydroxyl group, a nitro group, an oxy (aliphatic) group, an oxy(aliphatic)hydroxyl group, an oxy (alkyl)hydroxyl group, an oxycarbonyl group, an oxysulfonyl group, a perfluoroalkyl group, a phosphate group, a saccharide group, a sulfamoyl group, a sulfonamido group, a sulfonylamino group, a sulfonyl group, a sulfoxide group, a thio group, a thioalkaryl group, a thioaralkyl group, a trifluoroalkyl group, or an ureido group. Any of the above-mentioned groups may be further substituted with at least one substituent, such as with a halogen, sulfonyl, or phosphate moiety. However, to improve the stability of the phosphazene ionic liquid at high temperature and high cell voltage, the phosphazene ionic liquid may not include a halogen atom directly bonded to a phosphorus atom of the phosphorus-nitrogen unit.

In embodiments of the disclosure in which the ionic charge is present on the terminal portion of the pendant group, the pendant group ($R_4$ in FIG. 2D) may include a positively charged group or moiety bonded to the phosphorus atom through a heteroatom. The heteroatom may be an oxygen atom, a sulfur atom, or a phosphorus atom. For convenience, this pendant group is referred to herein as the "charged pendant group" or "positively charged pendant group." At least one of the pendant groups may include a positive charge at the portion distal to the phosphorus-nitrogen unit such that the positive charge is distanced or separated from the phosphorus-nitrogen unit, such as from the phosphazene ring of a cyclic phosphazene compound. While FIG. 2D illustrates a phosphazene ionic liquid having one charged pendant group, the phosphazene ionic liquid may include a plurality of charged pendant groups. Furthermore, while FIG. 2D illustrates $R_4$ as the charged pendant group, $R_1$-$R_3$, $R_5$, or $R_6$ may be the charged pendant group. The atom providing the positive charge to the pendant group may be distanced or separated from the phosphorus atom of the phosphazene ring by at least one atom in addition to being at the terminal portion of the pendant group. Each of the remaining pendant groups ($R_1$-$R_3$, $R_5$, and $R_6$ in FIG. 2D) is independently selected from one of the previously described groups. The charged portion of the charged pendant group may be bonded to the heteroatom through a linker group, such as a hydrocarbon linker group. By way of example, the linker group may include from 1 carbon atom to 5 carbon atoms. By utilizing a short linker group (e.g., a linker group having a low molecular weight), the molecular weight of the charged pendant group may be low, producing the phosphazene ionic liquid exhibiting a low overall molecular weight and low viscosity.

The charged group on the terminal portion of the pendant group may be an ionic form of an aromatic amine, an aryl amine, or an aliphatic amine, such as a nitrogen-containing aryl group, a primary amine, a secondary amine, or a tertiary amine. The aromatic amine may be an aniline group. The nitrogen-containing aryl group may include, but is not limited to, a pyrrole group, an imidazole, a pyrazole, a pyridine group, a pyrazine group, a pyrimidine group, or a pyridazine group. In one embodiment, the charged group is a pyridinium group. By way of example, the amine group may be a methyl amino group or a dimethyl amino group. In one embodiment, the charged group is a dimethyl amino group. In one embodiment, the charged pendant group is a dimethyl amino propanoxy group. In another embodiment, the charged pendant group is a 4-pyridine propanoxy group.

The anionic portion of the phosphazene ionic liquid may be an organic or inorganic anion that is configured to form a salt with the cationic portion of the phosphazene ionic liquid. The anionic portion of the phosphazene ionic liquid may be a lithium-ion-type anion including, but not limited to, tetrafluoroborate ($BF_4^-$), hexafluorophosphate ($PF_6^-$), bis(oxalate) borate ($BOB^-$), hexafluoroarsenate ($AsF_6^-$), hexafluoroantimonate ($SbF_6^-$), tetrachloroaluminate ($AlCl_4^-$), hydrogen sulfate ($HSO_4^-$), perchlorate ($ClO_4^-$), mesylate ($CH_3SO_3^-$), chloride ($Cl^-$), bromide ($Br^-$), iodide ($I^-$), an alkyl halide, or a perhalogenated alkyl halide of a group VA element. Other anionic species may also be used, such as trifluoromethanesulfonyl imide ($N(SO_2CF_3)_2^-$), trifluoromethanesulfonate ($CF_3SO_3^-$), or trifluoroacetate ($CF_3CO_2^-$). The anion may be selected such that the phosphazene ionic liquid is a liquid at the intended use temperature (e.g., operation temperature). The anion may also provide the phosphazene ionic liquid with sufficient electrochemical stability for use in the energy storage device. If the phosphazene ionic liquid is to be used as an additive in the electrolyte solution, a common anion, such as chloride, may be paired with the cationic portion of the phosphazene ionic liquid.

Phosphazene ionic liquids having a positive charge on the phosphorus or nitrogen atoms of the phosphorus-nitrogen unit may be synthesized by converting a non-ionized precursor compound to an ionized compound. The non-ionized precursor compound may have the desired pendant groups bonded to the phosphorus or nitrogen atoms of the phosphorus-nitrogen unit. The non-ionized precursor compound may be converted to the phosphazene ionic liquid by conventional techniques, which are not described in detail herein.

The phosphazene ionic liquid including the charged pendant group may be formed by synthesizing a non-ionized precursor compound having the desired pendant groups, including the pendant group(s) which ultimately becomes ionized, bound to the phosphorus or nitrogen atoms. The non-ionized precursor compound may be formed by conventional techniques, which are not described in detail herein. By way of example, if the phosphazene ionic liquid is a six-membered cyclic compound, the non-ionized precursor compound may be synthesized by a nucleophilic substitution reaction of at least one organic nucleophile with poly[bis-chlorophosphazene]. The poly[bis-chlorophosphazene] may be synthesized by a ring opening polymerization of hexachlorocyclotriphosphazene (also known as phosphonitrilic chloride trimer), which is commercially available, such as from Sigma-Aldrich Co. (St. Louis, Mo.). The ring opening polymerization, which produces a linear polymer from the hexachlorocyclotriphosphazene is conducted by conventional techniques and, therefore, is not described in detail herein. The desired pendant group(s) for the non-ionized precursor compound may be bonded to the phosphorus atoms of the poly[bis-chlorophosphazene] by a nucleophilic substitution reaction between the poly[bis-chlorophosphazene] and at least two organic nucleophiles containing the desired pendant group(s). One of the organic nucleophiles may be a precursor of the one or more of the pendant group(s) to be bonded to the phosphorus atoms, while the other organic nucleophile may be a precursor of the remaining pendant groups to be bonded to the phosphorus atoms. The organic nucleophiles may be reacted with the phosphorus atoms of the poly[bis-chlorophosphazene], with each of the organic nucleophiles including one of the desired pendant groups of the non-ionized precursor compound. By adjusting the relative amounts of the different organic nucleophiles and the reaction conditions, such as temperature and pressure, the desired pendant groups may be bonded to the phosphorus atoms of the phosphazene compound. A desired amount of a first organic nucleophile that includes a first pendant group may be reacted with the phosphorus atom of the poly[bis-chlorophosphazene] and heated to ensure all of the first organic nucleophile reacts. An excess of a second organic nucleophile that includes a second pendant group may then be added to the reaction mixture of the poly[bis-chlorophosphazene] and the first organic nucleophile and heated until all the chlorine atoms of the poly[bis-chlorophosphazene] have been replaced with the desired nucleophilic pendant groups.

The non-ionized precursor compound may be ionized by exposure to a reagent containing the anionic group. By way of example, the non-ionized precursor compound may be exposed to an acid, such as a mineral acid (i.e., an inorganic acid), which ionizes the terminal nitrogen atom of the pendant group and forms the phosphazene ionic liquid including the cationic portion and the anionic portion. Depending on the desired anionic portion of the phosphazene ionic liquid, the mineral acid may be hydrochloric acid (HCl), hydrofluoric acid (HF), hydrobromic acid (HBr), nitric acid ($HNO_3$), or combinations thereof. Alternatively, the non-ionized precursor compound may be exposed to methyl iodide (MeI), which ionizes the terminal nitrogen atom of the pendant group and forms the phosphazene ionic liquid including the cationic portion and the anionic portion. Thus, the non-ionized precursor compound is converted to the phosphazene ionic liquid having the at least one charged pendant group. Without being bound by theory, the conversion of the non-ionized precursor compound to the phosphazene ionic liquid may reduce the tendency of the phosphazene compound to associate with lithium due to cation-cation repulsion. This reduction in solvent-ion association may improve lithium mobility and reduce overall electrolyte viscosity. Without being bound by theory, the nitrogen atoms in non-ionized phosphazene compounds have affinity for lithium. By utilizing a charged phosphazene compound (e.g., a phosphazene ionic liquid of an embodiment of the disclosure), repulsion occurs between the positive charge of the phosphazene ionic liquid and the lithium ions, reducing the energetic cost of lithium desolvation under conditions of electrochemical cell operation.

The phosphazene ionic liquid may be used as an additive in an electrolyte solution or as a primary solvent in the electrolyte solution. If the phosphazene ionic liquid is used as the additive, the phosphazene ionic liquid may be present in the electrolyte solution at from approximately 1% by weight (wt %) to approximately 40 wt %, such as from approximately 1 wt % to approximately 10 wt %. If the phosphazene ionic liquid is used as the primary solvent, the phosphazene ionic liquid may be present in the electrolyte solution at greater than approximately 40% by volume, such as greater than approximately 40 wt % to approximately 100 wt %. The electrolyte solution including the phosphazene ionic liquid may be used as a battery solvent in an energy storage device, such as a lithium battery, capacitor, ultracapacitor, or supercapacitor. The term "lithium battery" means and includes a lithium ion battery or a lithium metal battery, each of which is known in the art and, therefore, is not described in detail herein. The energy storage device may be used by way of non-limiting example in a vehicle, such as a car (private, commercial, fleet, or military), an aircraft, or a watercraft. The energy storage device may be a replacement for conventional nickel-metal hydride batteries, lead-acid batteries, or nickel-cadmium batteries. The electrolyte solution may also include a mixture of phosphazene ionic liquids according to embodiments of the disclosure.

Figure 3:
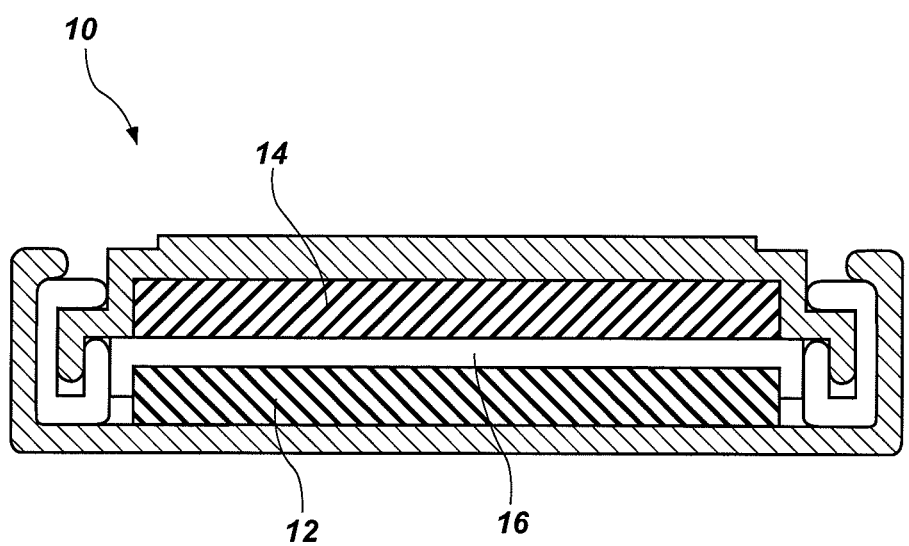
FIG. 3 is a schematic illustration of a cross-sectional view of an energy storage device including a phosphazene ionic liquid according to embodiments of the disclosure.

The electrolyte solution including the phosphazene ionic liquid may be used in the energy storage device 10 (e.g., a battery) that includes a positive electrode 12 (e.g., a cathode), a negative electrode 14 (e.g., an anode), and a separator 16 between the electrodes 12, 14, as shown in FIG. 3. The electrolyte solution may be positioned in the separator 16 but is in contact with at least one of the positive electrode 12 and the negative electrode 14. The phosphazene ionic liquid may account for substantially all of the electrolyte solution, such as approximately 90% of the electrolyte solution, if the viscosity of the phosphazene ionic liquid is sufficiently low. The phosphazene ionic liquid may also be used an additive in the electrolyte solution. If used as an additive, the phosphazene ionic liquid may be present at from approximately 1% to approximately 10% of a total volume of the electrolyte solution. By way of example, the energy storage device 10 may be a lithium battery containing the electrolyte solution. The electrolyte solution including the phosphazene ionic liquid of the disclosure may exhibit a higher stability and longer cycle life than conventional electrolyte solutions.

The electrolyte solution may be prepared by dissolving the phosphazene ionic liquid in a solvent that is stable at the operation temperature and operation voltage of the energy storage device 10. When the phosphazene ionic liquid is dissolved, the electrolyte solution is configured to function as a liquid that carries electricity in the energy storage device. The solvent may be a water-miscible solvent, such as ethylene carbonate (EC) or ethyl methyl carbonate (EMC), a low molecular weight organic solvent, such as an organic carbonate, an ester, an ether, a siloxane, or combinations thereof. The solvent may have a molecular weight of less than 150. The solvent may account for from approximately 1 wt % to approximately 90 wt % of the electrolyte solution, such as from approximately 10 wt % to approximately 70 wt % of the electrolyte solution. The phosphazene ionic liquid may account for from approximately 1 wt % to approximately 90 wt % of the electrolyte solution.

The following examples serve to explain embodiments of the disclosure in more detail. These examples are not to be construed as being exhaustive or exclusive as to the scope of this disclosure.

EXAMPLES

Example 1

Synthesis of PhIL1, PhIL2, and PhIL3

Sodium, 4-pyridine propanol, methylene chloride, methyl iodide, diethyl ether, and sodium hydride (NaH) were obtained from Sigma-Aldrich Chemical Co. and used as received. Phosphonitrilic chloride trimer was obtained from SAFC Global, a division of Sigma-Aldrich Chemical Co., and purified via sublimation prior to use. Ethanol and 1,4-dioxane were received from Sigma-Aldrich Chemical Co. as anhydrous grade and used as received. Schlenk techniques were employed and the reactions continuously blanketed with dried nitrogen gas into an oil bubbler. Solvents were introduced to dried glassware employing cannulae and sterile syringes were used to add reactive reagents. Reaction progress was monitored with $^{31}$P nuclear magnetic resonance (NMR) and molecular structure was verified using $^{31}$P, $^{13}$C, and $^{1}$H NMR techniques.

Figure 4:
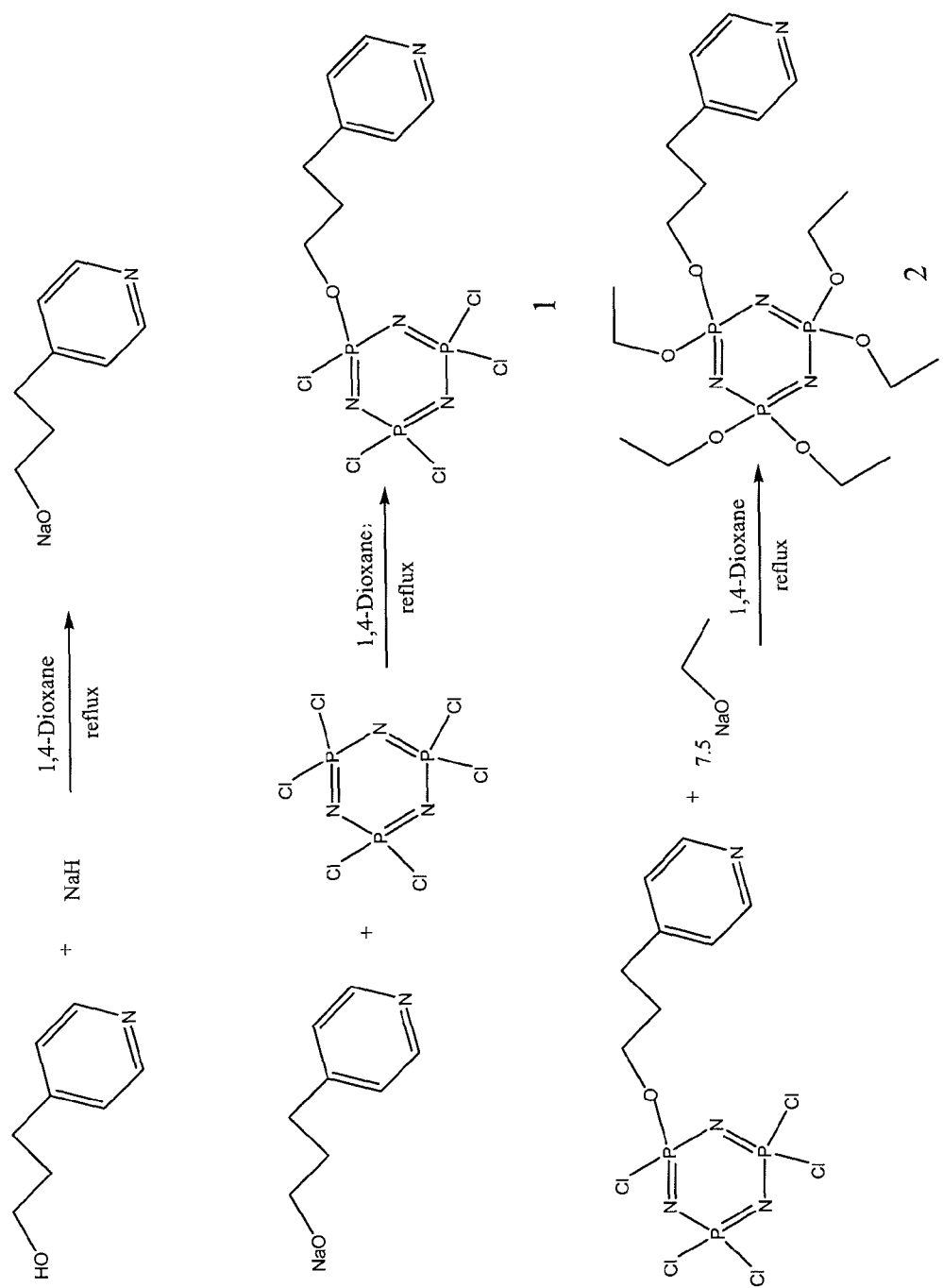
FIG. 4 illustrates a synthesis of a non-ionized precursor compound of a phosphazene ionic liquid according to an embodiment of the disclosure.
Figure 5:
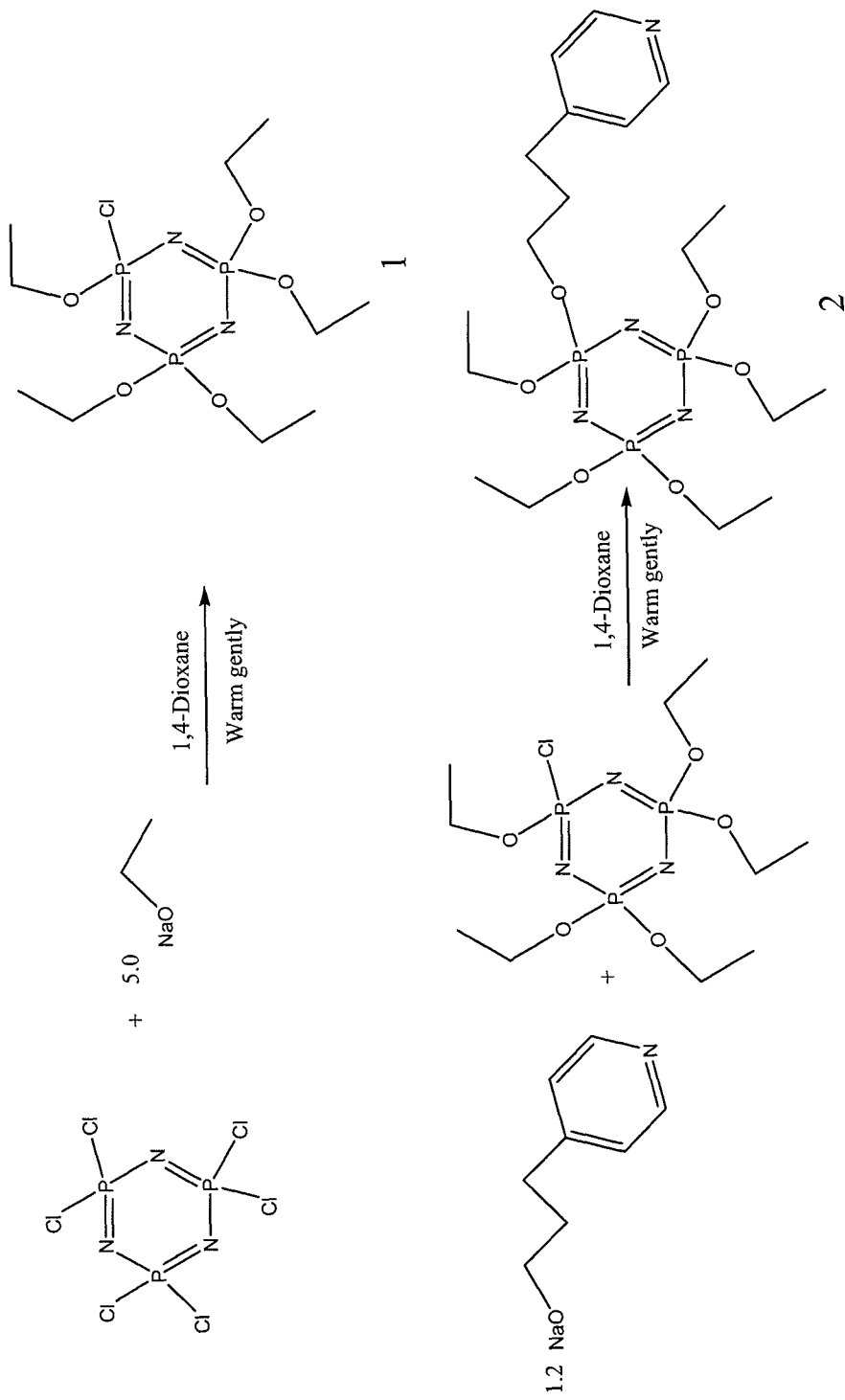
FIG. 5 illustrates a synthesis of another non-ionized precursor compound of a phosphazene ionic liquid according to an embodiment of the disclosure.

Two methods of forming intermediate 2 are shown in FIGS. 4 and 5. Intermediate 2 is acidified or reacted with methyl iodide to form the phosphazene ionic liquids PhIL1 and PhIL2 as shown in FIG. 6.

One method of forming intermediate 2 is shown in FIG. 4. To a pre-dried three-neck flask, 4-pyridine propanol (10 g) was added and purged with dry nitrogen. The flask was fitted with a dried reflux condenser and to an outlet to the oil bubbler. The remaining neck was fitted with a septum stopper to facilitate the addition of reagents and solvents. Anhydrous 1,4-dioxane (200 ml) was added by cannulae. Dry NaH (1.75 g, 95%) was added and the solution was gently heated for three hours. Phosphonitrilic chloride trimer (25 g) was dissolved in 100 ml dioxane at room temperature and was added to the pyridine propanol solution. After 45 minutes of gently heating, the solution was allowed to cool overnight to produce intermediate 1. This solution was added to an excess of sodium ethoxide in dioxane in a three-neck flask assembled as described above (previously prepared from 10.3 g Na and excess ethanol) and the solution gently heated. Reaction progress was followed by $^{31}$P NMR until substitution of the phosphazinic chlorides was complete. The competed reaction containing intermediate 2 was allowed to cool to room temperature before workup commenced. The excess sodium ethoxide in the reaction was quenched with 200 ml of water and transferred into a 2 L separation funnel. Methylene chloride (1 L) was added to the funnel and the funnel agitated. One phase was formed. The volume of the solution was reduced by two-thirds and two phases were formed. Intermediate 2 was obtained through the retention of the organic phase, purified via successive washings with nanopure water, and dried via rotary evaporation.

A second method of forming intermediate 2 is shown in FIG. 5. Ethanol (19.0 ml) was added to a pre-dried three-neck flask and purged with dry nitrogen. The flask was fitted with a dried reflux condenser and to an outlet to the oil bubbler. The remaining neck was fitted with a septum stopper to facilitate the addition of reagents and solvents. Anhydrous 1,4-dioxane (200 ml) was added by cannulae. Metallic sodium (7.64 g) was added and the solution was gently warmed until the sodium was consumed, producing a sodium ethoxide solution. Phosphonitrilic chloride trimer (23.1 g) was dissolved in 100 ml dioxane at room temperature and added to the sodium ethoxide solution to produce intermediate 1. After five hours of gently heating, the solution was allowed to cool overnight. 4-pyridine propanol (11.88 g) was added to a separate pre-dried three-neck flask and purged with dry nitrogen. The flask was fitted with a dried reflux condenser and to an outlet to the oil bubbler. The remaining neck was fitted with a septum stopper to facilitate the addition of reagents and solvents. Anhydrous 1,4-dioxane (300 ml) was added by cannulae. Dry NaH (2.07 g, 95%) was added and the solution was gently warmed overnight. The 4-pyridine propanol solution was added to the cooled sodium ethoxide solution and gently heated for five hours. Heat was removed from the reaction, which was allowed to stir overnight. The excess alkoxide was quenched via the addition of 350 ml of water and then neutralized with 2.0 M HCl. The solvent (approximately two-thirds of the volume) was removed by rotary evaporation to yield a biphasic solution. The top phase was a dioxane-rich solution containing intermediate 2. The top phase was separated and the solvent removed by rotary evaporation to yield a dark water-immiscible oil, which was washed successively with portions of nanopure water to remove residual salts and excess pyridine propanol, producing intermediate 2.

Figure 6:
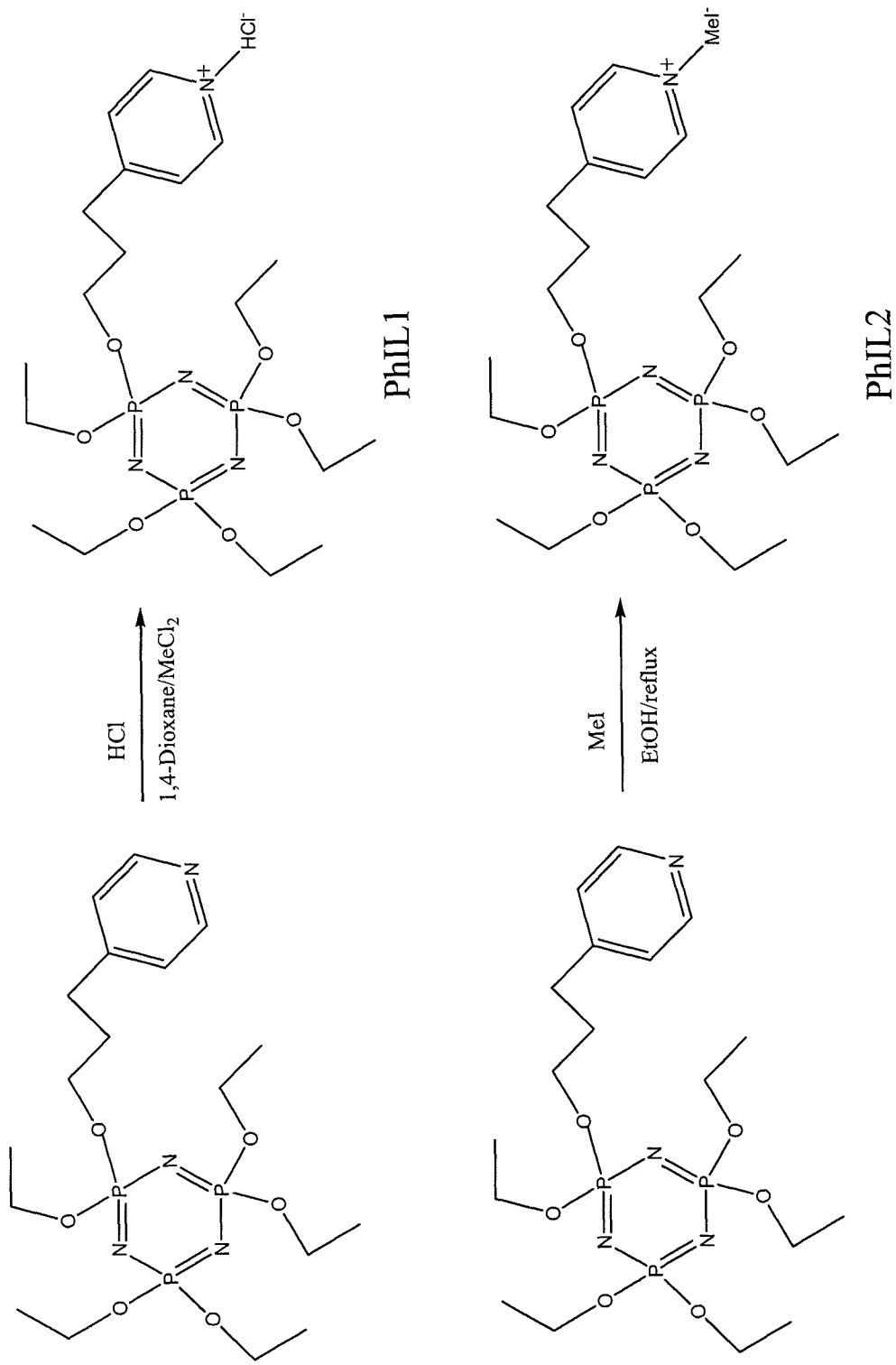
FIG. 6 illustrates a synthesis of phosphazene ionic liquids according to embodiments of the disclosure.

As shown in FIG. 6, PhIL1 was obtained from intermediate 2 by the slow addition of excess HCl (2.0 M HCl), forming a third phase. This phase was removed and reduced to an oil via rotary evaporation. The oil was purified by taking the oil into a fresh aliquot of methylene chloride and successively washing with water. As shown in FIG. 6, PhIL2 was obtained by mixing an aliquot of intermediate 2 with ethanol and adding an excess of methyl iodide. The solution was refluxed for five hours and the product precipitated with diethyl ether.

Figure 7:
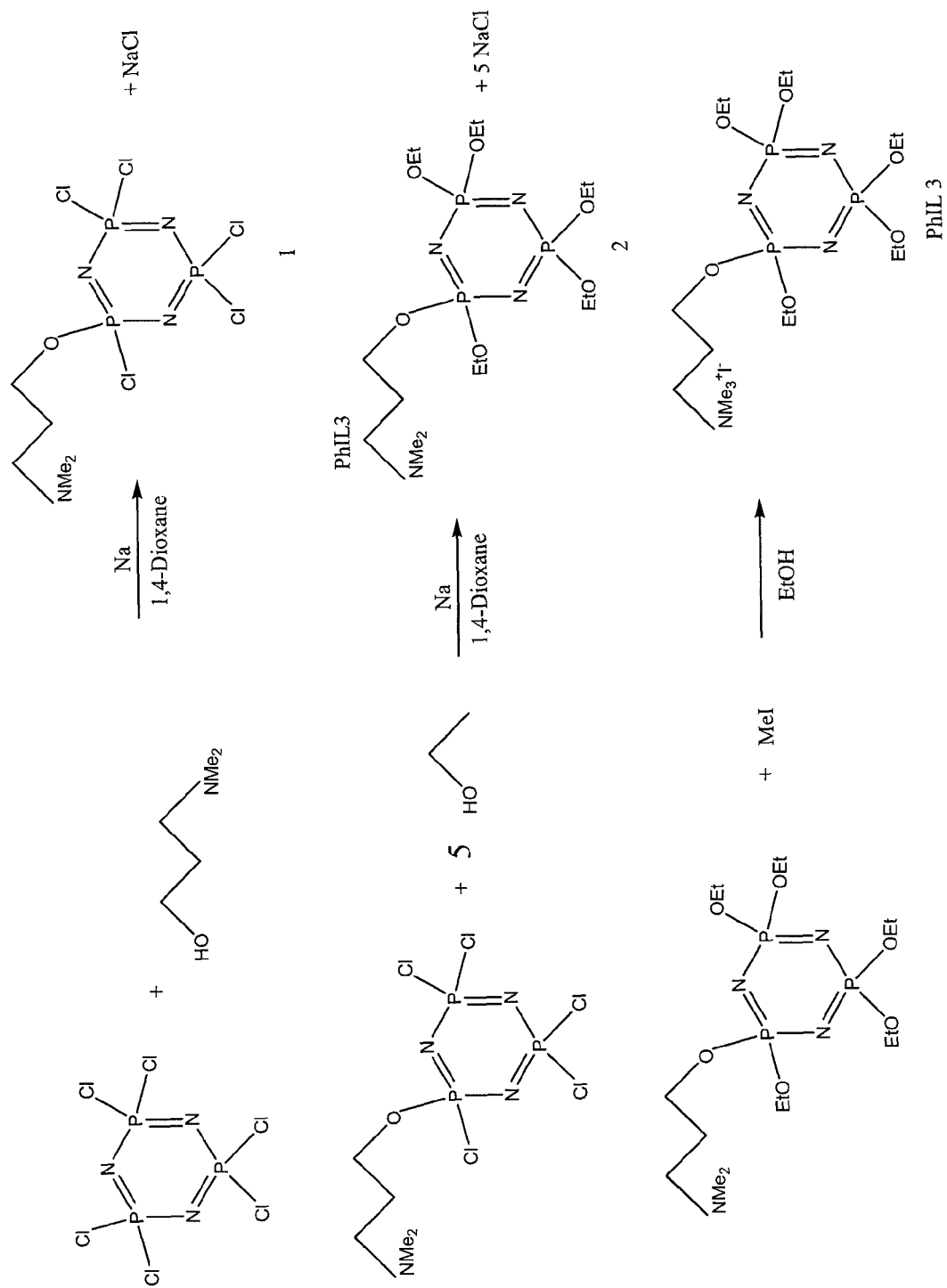
FIG. 7 illustrates a synthesis of yet another non-ionized precursor compound and phosphazene ionic liquid according to an embodiment of the disclosure.

A method of synthesizing PhIL3 is shown in FIG. 7. Anhydrous 1,4-dioxane was added to 3-dimethylamino-1-propanol to form a 3-dimethylamino-1-propanol solution. Metallic sodium was added and the solution gently warmed until the sodium was consumed. Phosphonitrilic chloride trimer was dissolved in dioxane at room temperature and was added to the 3-dimethylamino-1-propanol solution to produce intermediate 1. After five hours of gently heating, the solution was allowed to cool overnight. Ethanol, metallic sodium, and anhydrous 1,4-dioxane (300 ml) were converted to the sodium ethoxide reagent and then added to the solution and reacted to form intermediate 2. Intermediate 2 was purified by sequential bicarbonate/water extraction in methylene chloride. Intermediate 2 was then reacted with methyl iodide to produce PhIL3.

Example 2

Characterization of PhIL1 and Saturated PhIL1 (PhIL1A)

The conductivity, viscosity, flashpoint, and lithium salt loading levels were determined for PhIL1. All solvents were dried in a vacuum/argon oven at 60° C. and 75 Torr argon for one week and maintained in an argon drybox prior to use. The conductivity was measured with a TOA CM-30R conductivity meter and all measurements were taken on dried solvents in an argon drybox. A series of ten sequential experiments were taken and averaged to yield the reported value. Viscosity measurements were taken on a Cambridge Instruments falling bob viscometer. Again, all measurements were made on dried solvents and performed in an argon drybox. A series of eight sequential experiments were taken and averaged to yield the reported value. Flash points were measured with a SETAFLASH® Series 8 closed cup flash point analyzer. Work was performed on the benchtop using a single ramp method at temperatures starting above 100° C. Room temperature saturation $LiPF_6$ solutions were prepared in an argon drybox using dried PhIL1. The PhIL1 was saturated with $LiPF_6$ to produce PhIL1A. An excess of battery grade $LiPF_6$ (obtained from Sigma-Aldrich Chemical Co., used as received, opened and maintained only in an argon drybox) was added to an aliquot of PhIL1. The mixture was stirred via magnetic stirring at ambient temperature for three days. The solution was settled and the salted solvent carefully decanted into a separate vessel. This salted solution was also maintained in an argon drybox until used for the stated characterization experiments. The salted PhIL1 (2.0 g), which is referred to as PhIL1A, was digested in KOH saturated ethanol for one week. The digested sample in KOH/ethanol was then diluted for analysis by ICP-OES. The concentration of $LiPF_6$ in PhIL1A was determined to be 0.196 M. Characterization data for PhIL1 and PhIL1A are reported below:

|       | Viscosity | Conductivity | Flash Point |
|-------|-----------|--------------|-------------|
| PhIL1 | 65.0 cP   | 135 μS/m     | 184° C.     |
| PhILA | 126 cP    | 504 μS/m     | N/A         |

PhIL1 was tested in rechargeable lithium-ion coin cells, such as 2032-type coin cells. PhIL1 was used at additive levels within the electrolyte solution, and its performance measured in terms of cell capacity and impedance. Overall results show that PhIL1 provided benefits in slowing aging processes in the test cells, and yielded cell impedances generally lower than those obtained with non-ionic phosphazene compounds.

Example 2

Density Functional Theory (DFT) Simulations

Figure 8:
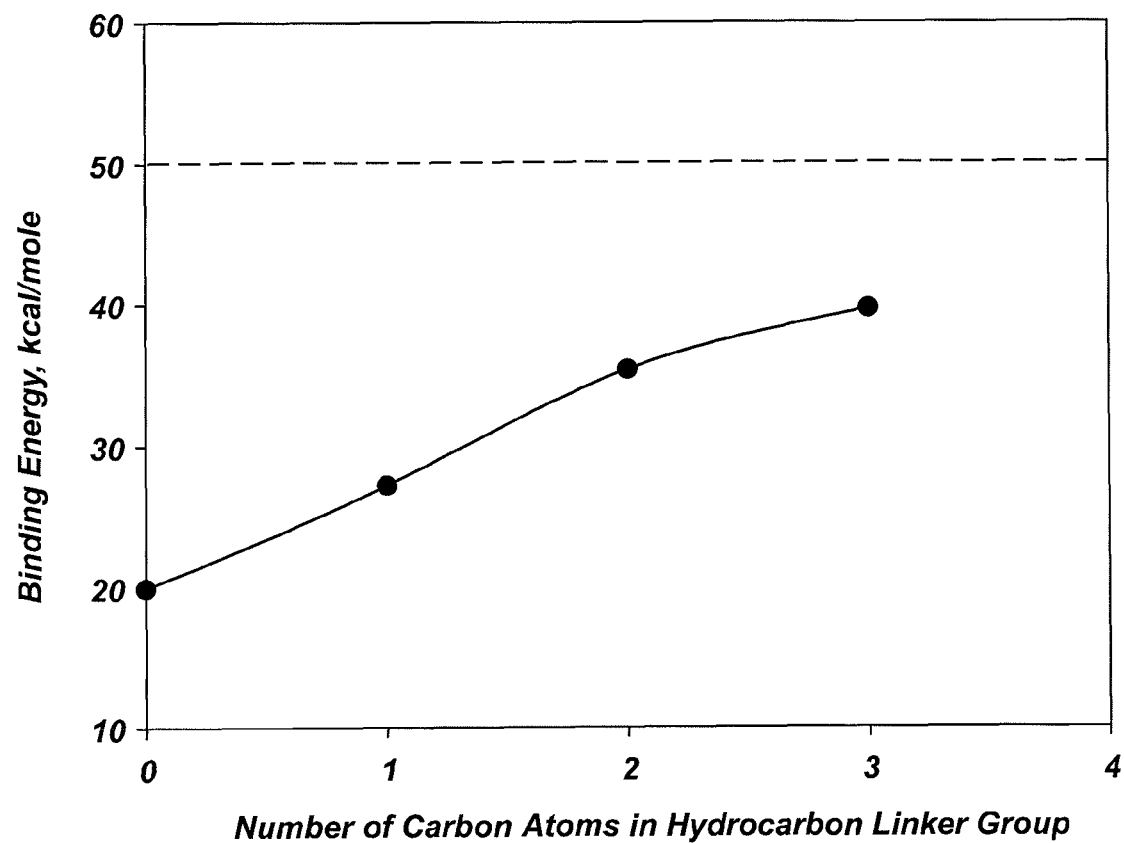
FIG. 8 is a graph showing the nitrogen to lithium binding energy as a function of the number of carbon atoms in a hydrocarbon linker group of a phosphazene ionic liquid according to an embodiment of the disclosure.

Density Function Theory (DFT) calculations were performed to investigate the solvent-to-lithium binding energy (the binding energy between nitrogen atoms of the phosphazene ring and lithium cations) for PhIL1 and PhIL1-like compounds. The number of carbon atoms in the hydrocarbon linker of the pyridinium pendant group was varied between zero carbon atoms and 3 carbon atoms to determine the effect on the interactions between the nitrogen atoms in the phosphazene ring and lithium cations. The DFT calculations were performed with Gaussian 03, B3LYP/6-311G(d,p) basis set. All structures are minima (no imaginary frequencies). The nitrogen to lithium binding energy as a function of the number of carbon atoms in the hydrocarbon linker group is shown in FIG. 8. The dashed line at 50 kcal/mole indicates the nitrogen to lithium binding energy of single-ligand binding for ethylene carbonate (EC):$Li^+$.

The DFT calculations demonstrated a reduction in the energy of interaction to a level less than that of EC. The reduced binding energy enables lower energy barriers for lithium desolvation, and promotes lower charge transfer impedance.

Example 3

Use of PhIL1 in Rechargeable Lithium-Ion Cells

PhIL1 (as paired with a chloride anion) was tested in a 2032-type coin cell having one of two anode/cathode pairs as a 3% additive in the baseline electrolyte described below. One anode/cathode pair is $LiNi_{0.5}Mn_{1.5}O_4/Li_4Ti_5O_{12}$ (LNMO/LTO), having a voltage range of 2.0 V to 3.35 V and a rated capacity estimated at 1.536 $mAh/cm^2$ (C/1), and the other anode/cathode pair is $LiNi_{1/3}Mn_{1/3}Co_{1/3}O_2$/graphite (NMC/Carbon), having a voltage range of 3.0 V to 4.2 V and a rated capacity of 2.4 $mAh/cm^2$ (C/25). The assembled cells underwent conventional formation cycling to produce protective passivation films, then completed a matrix of cycling rates to investigate both cell polarization and aging. A 'C' rate is defined here as the rated energy capacity, generally the discharge capacity, attainable in fully discharging a cell in one hour (C/1 reference). Thus, C/10 would represent a 10-hour discharge at a current one-tenth that of the C/1 reference, while 3C would elapse in a 20-minute discharge at a current three times that of the C/1 reference. All cells underwent electrochemical impedance spectroscopy (EIS) before and after the cycling protocol. The testing protocol included formation cycling (C/10 @ 3), EIS, followed by a matrix of C/10, C/3, C/1, and 3C, all at 30° C. Testing concluded with 3C cycling at 55° C. to determine how the additives affected high temperature tolerance of the electrolyte solution.

Figure 9:
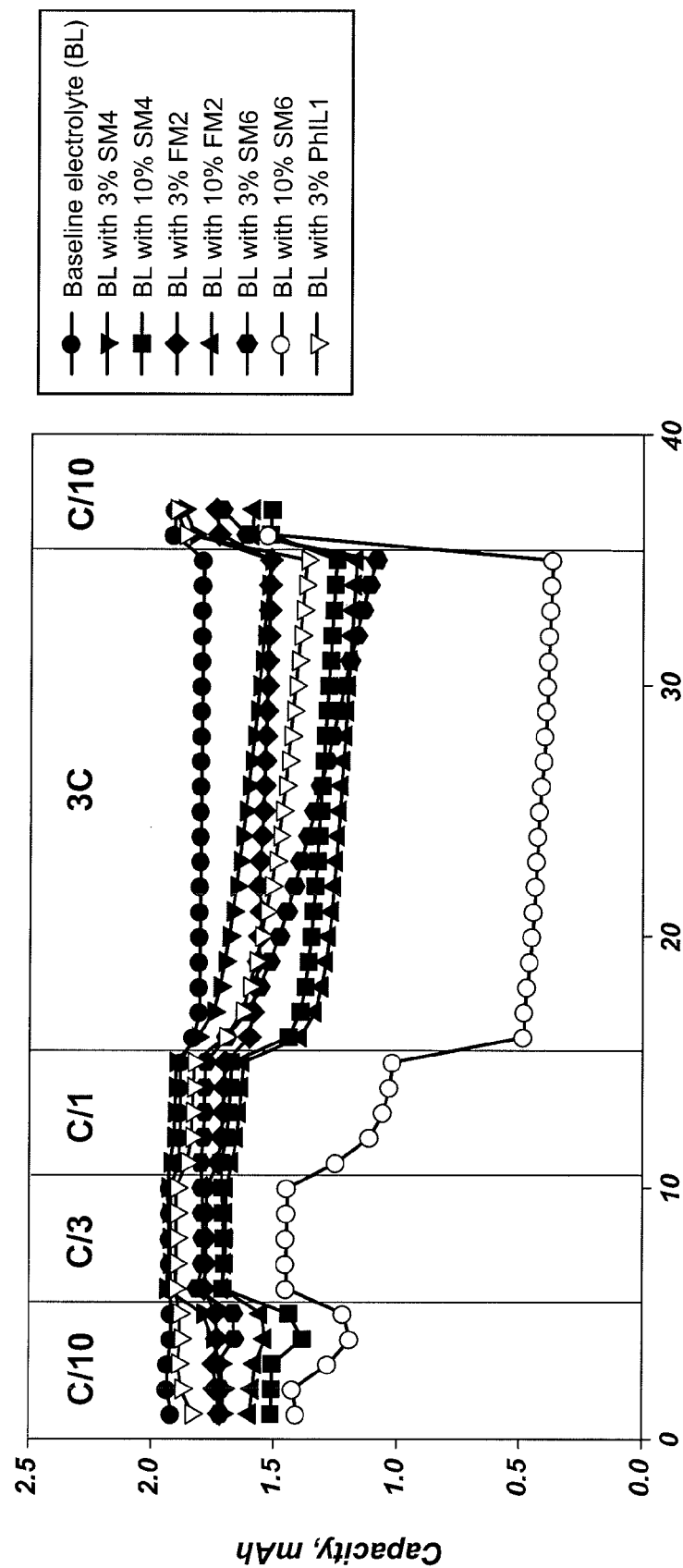
FIG. 9 is a graph showing capacity results for a phosphazene ionic liquid according to an embodiment of the disclosure.

The electrolyte solutions included a baseline electrolyte (BL) as a control and electrolyte solutions including a phosphazene ionic liquid or other phosphazene compound. The baseline electrolyte (BL) included ethylene carbonate (EC) and ethyl methyl carbonate (EMC) (2:8 volume ratio) and 1.2 M $LiPF_6$. The other electrolyte solutions included the indicated portion of additive (phosphazene ionic liquid or other phosphazene compound) in the baseline electrolyte (BL). The SM4, SM6, and FM2 electrolyte solutions include non-ionic phosphazene compounds as the additive and are included for comparison. The capacity results for the 2032-type coin cells having a LNMO/LTO anode/cathode pair are shown in FIG. 9. The coin cells with 3% PhIL1 showed the highest capacity at the conclusion of the cycling suite, compared to the other phosphazene additives. Using PhIL1 as an additive exhibited good performance in the lithium-ion cells in terms of capacity retention and interfacial impedance.

Figure 10:
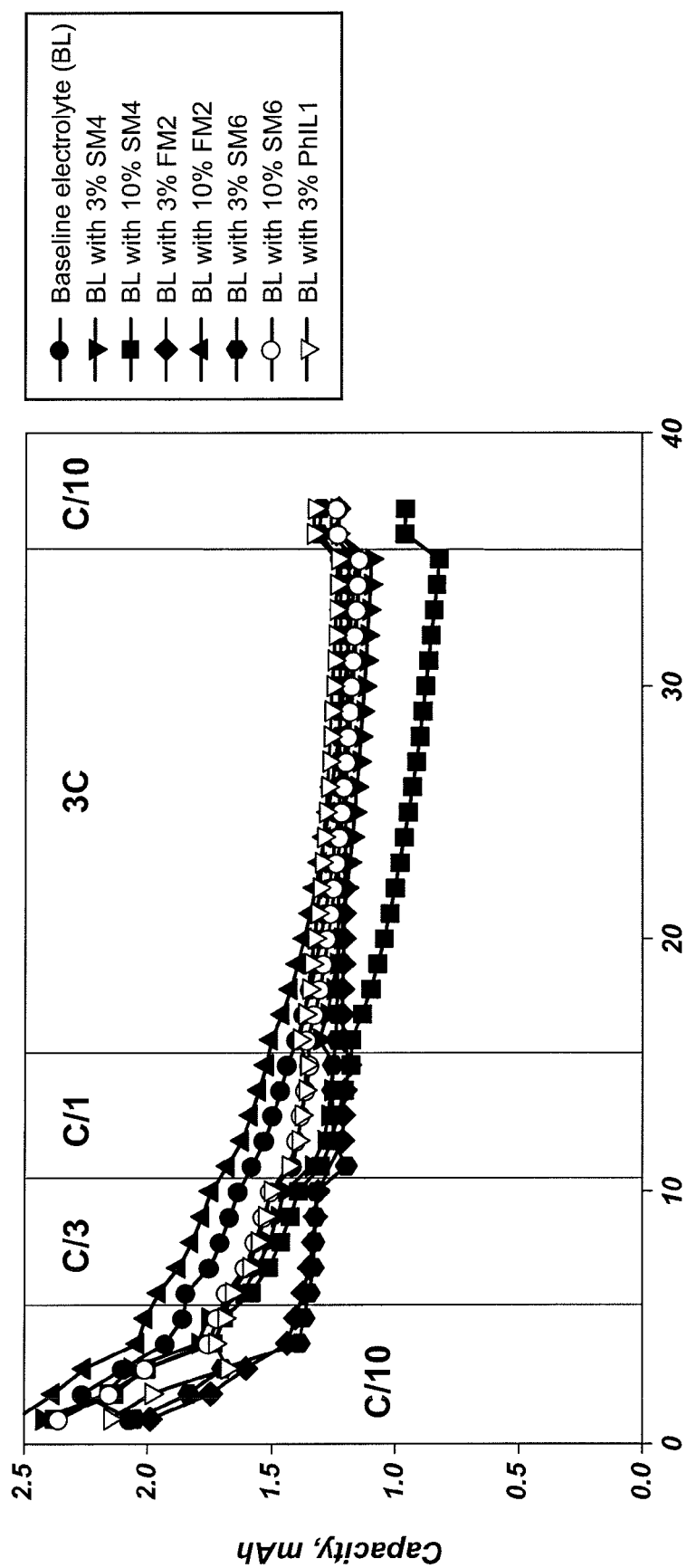
FIG. 10 is a graph showing capacity results for a phosphazene ionic liquid according to an embodiment of the disclosure.

Capacity results for the 2032-type coin cells having an NMC/Carbon anode/cathode pair are shown in FIG. 10. For this anode/cathode pair, coin cells with 3% PhIL1 show the highest capacity at the conclusion of the cycling suite, compared to other phosphazene additives and the baseline system.

Figure 11A:
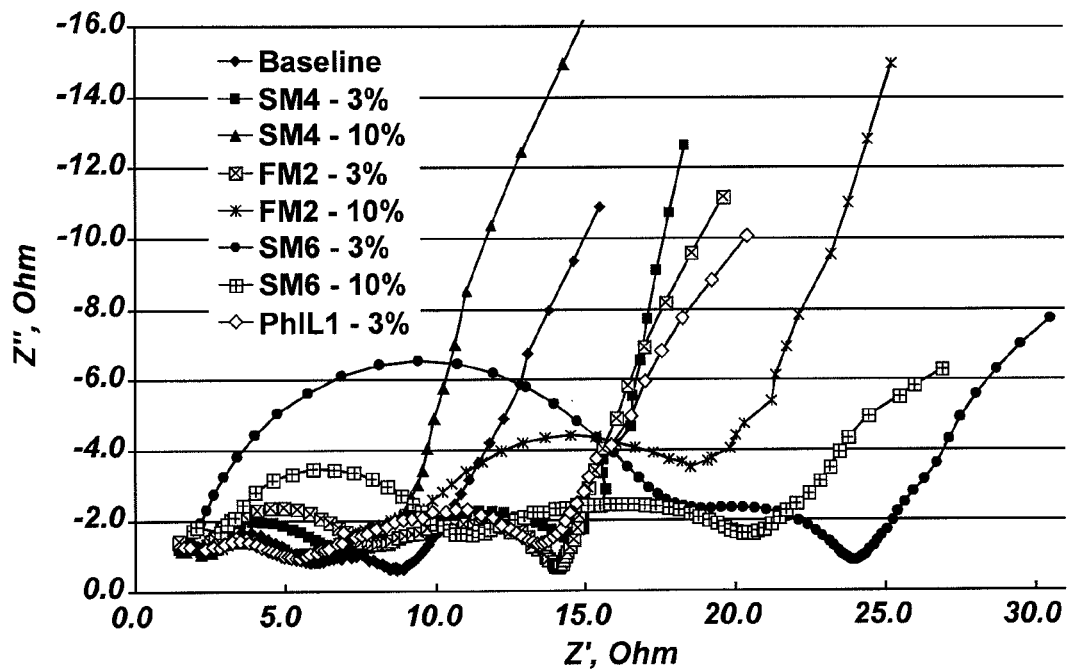
FIGS. 11A-11D are graphs showing interfacial impedance results for a phosphazene ionic liquid according to an embodiment of the disclosure.
Figure 11B:
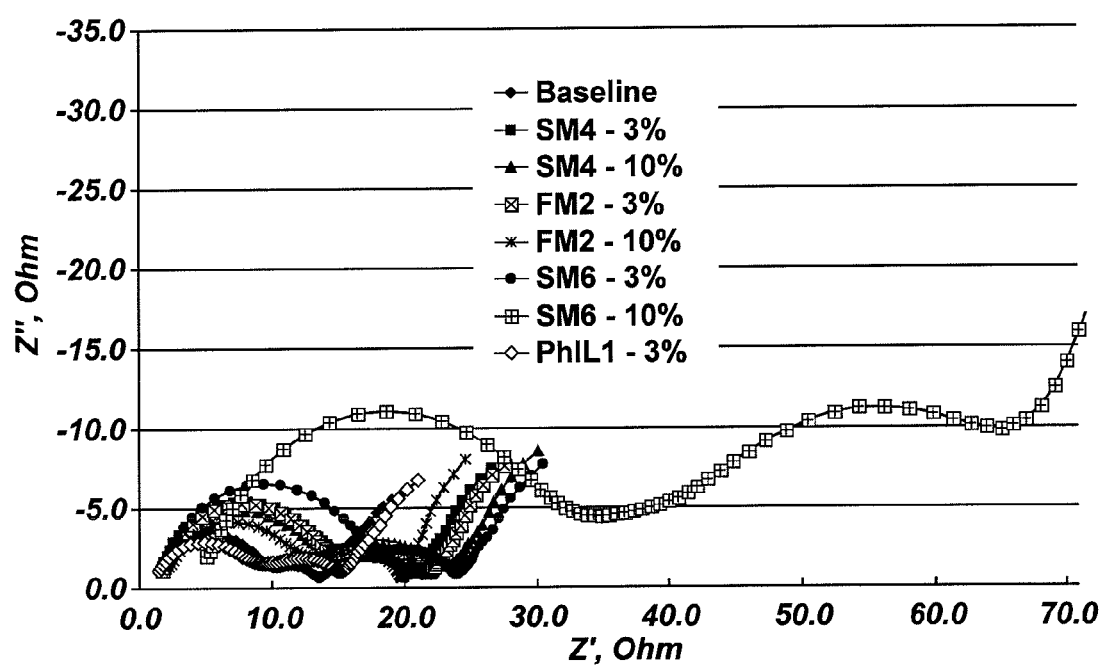
Figure 11C:
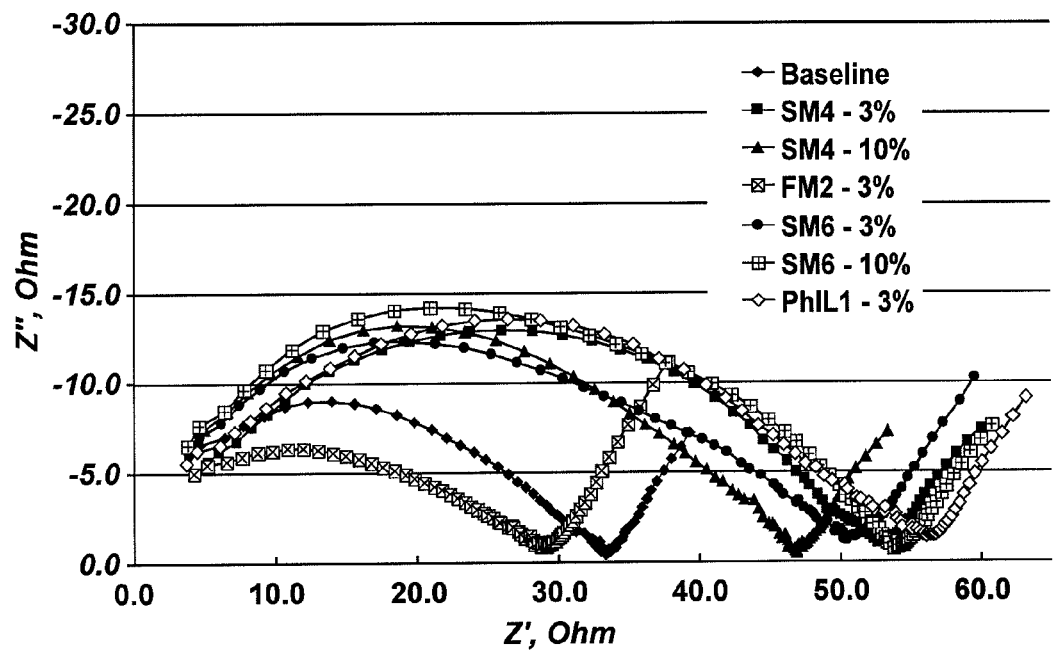
Figure 11D:
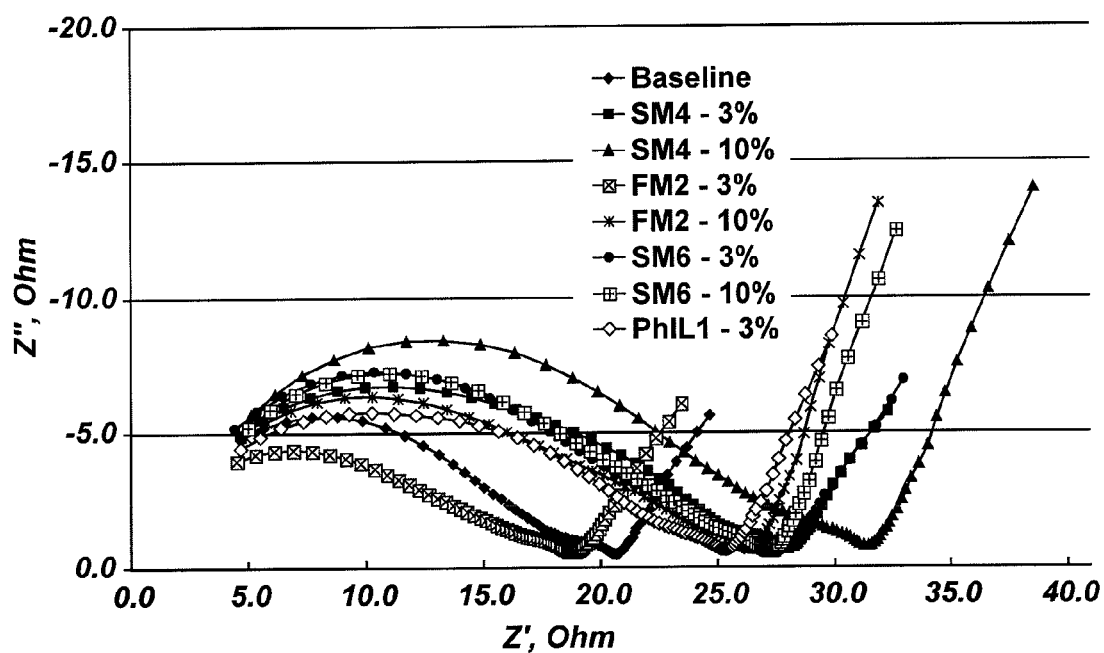

Interfacial impedance results are shown in FIGS. 11A and 11B for the LNMO/LTO anode/cathode pair and in FIGS. 11C and 11D for the NMC/Carbon anode/cathode pair. Cells with 3% PhIL1 generally showed lower interfacial impedance at the conclusion of the cycling suite, compared to the other phosphazene additives, which is in agreement with the capacity results described above. Thus, PhIL1 is a viable compound for use as an electrolyte solution in an energy storage device.

While the disclosure is susceptible to various modifications and alternative forms, specific embodiments have been shown by way of example in the drawings and have been described in detail herein. However, the disclosure is not intended to be limited to the particular forms disclosed. Rather, the disclosure encompasses all modifications, combinations, equivalents, and alternatives falling within the scope of the disclosure as defined by the following appended claims and their legal equivalents.

What is claimed is:
1. An ionic liquid, comprising:
    an ionic phosphazene compound comprising a plurality of phosphorus-nitrogen units and at least one pendant group bonded to each phosphorus atom of the plurality of phosphorus-nitrogen units, wherein a single pendant group of the at least one pendant group comprises a positively charged pendant group bonded to the phosphorus atom through an oxygen atom and the positively charged pendant group comprises a trimethyl amino propanoxy group or a 4-pyridine propanoxy group.

2. An ionic liquid, comprising:

an ionic phosphazene compound comprising a plurality of phosphorus-nitrogen units and at least one pendant group bonded to each phosphorus atom of the plurality of phosphorus-nitrogen units, wherein a single pendant group of the at least one pendant group comprises a positively charged pendant group and the positively charged pendant group is bonded to the phosphorus atom through an oxygen atom, a sulfur atom, or a phosphorus atom, the ionic phosphazene compound comprising the chemical structure

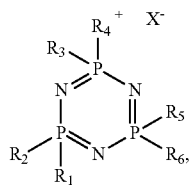

wherein each of $R_1$-$R_3$, $R_5$, and $R_6$ is a pendant group independently selected from the group consisting of hydrogen, an acyl group, an acylamino group, an acyloxy group, an alkyl group, an alkenyl group, an alkynyl group, an alkoxy group, an amino group, an alkylamino group, an alkylarylamino group, a dialkylamino group, an alkylthio group, an alkarylthio group, an aryl group, an arylamino group, a diarylamino group, an aryloxy group, an aralkyl group, an alkaryl group, an aralkoxy group, an alkaryloxy group, an arylthio group, an arylthio acyl group, an amino acid group, a carbamoyl group, a carbonamido group, a carboxyl group, a cyano group, a formyl group, a glycol group, a heteroalkyl group, a heteroaralkyl group, a heteroaryl group, a hydroxyl group, a nitro group, an oxy(aliphatic) group, an oxy(aliphatic)hydroxyl group, an oxy(alkyl)hydroxyl group, an oxycarbonyl group, an oxysulfonyl group, a perfluoroalkyl group, a phosphate group, a saccharide group, a sulfamoyl group, a sulfonamido group, a sulfonylamino group, a sulfonyl group, a sulfoxide group, a thio group, a thioalkaryl group, a thioaralkyl group, a trifluoroalkyl group, an ureido group, and a halogen-, sulfonyl-, or phosphate-substituted group thereof, $R_4$ comprises a positively charged primary aliphatic amine, a positively charged secondary aliphatic amine, a positively charged tertiary aliphatic amine, or a positively charged aryl amine and is bonded to the phosphorus atom of the phosphorus-nitrogen unit through the oxygen atom, the sulfur atom, or the phosphorus atom, and X is an anion independently selected from the group consisting of tetrafluoroborate, hexafluorophosphate, bis(oxalate)borate, hexafluoroarsenate, hexafluoroantimonate, tetrachloroaluminate, hydrogen sulfate, perchlorate, mesylate, chloride, bromide, iodide, an alkyl halide, a perhalogenated alkyl halide of a group VA element, trifluoromethanesulfonyl imide, trifluoromethanesulfonate, and trifluoroacetate and wherein the ionic phosphazene compound excludes

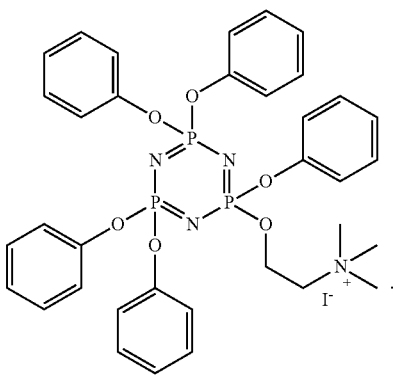

3. The ionic liquid of claim 2, wherein at least one of $R_1$-$R_3$, $R_5$, and $R_6$ does not comprise a halogen directly bonded to the phosphorus atom of the plurality of phosphorus-nitrogen units.

4. An ionic liquid, comprising:

an ionic phosphazene compound comprising a plurality of phosphorus-nitrogen units and at least one pendant group bonded to each phosphorus atom of the plurality of phosphorus-nitrogen units, wherein a single pendant group of the at least one pendant group comprises a positively charged pendant group and the positively charged pendant group is bonded to the phosphorus atom through an oxygen atom, the ionic phosphazene compound comprising:

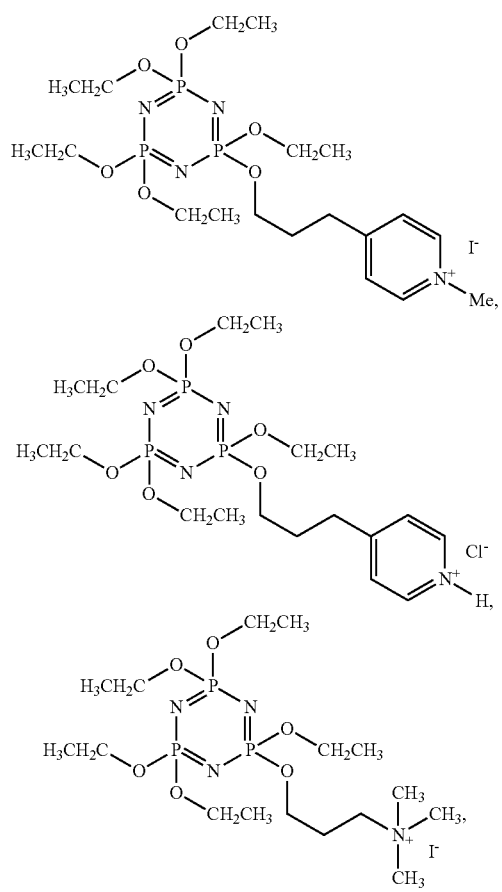

or combinations thereof.

5. An ionic liquid, comprising:
an ionic phosphazene compound comprising a plurality of phosphorus-nitrogen units and at least one pendant group bonded to each phosphorus atom of the plurality of phosphorus-nitrogen units, the ionic liquid comprising the chemical structure

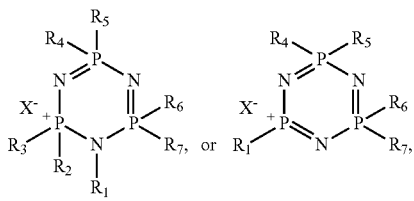

wherein each of $R_2$ and $R_3$ is a pendant group independently selected from the group consisting of an acyl group, an acylamino group, an acyloxy group, an alkenyl group, an alkynyl group, an alkoxy group, an amino group, an alkylamino group, an alkylarylamino group, a dialkylamino group, an alkylthio group, an alkarylthio group, an arylamino group, a diarylamino group, an aryloxy group, an aralkoxy group, an alkaryloxy group, an arylthio group, an arylthio acyl group, an amino acid group, a carbamoyl group, a carbonamido group, a carboxyl group, a cyano group, a formyl group, a glycol group, a heteroalkyl group, a heteroaralkyl group, a heteroaryl group, a hydroxyl group, a nitro group, an oxy (aliphatic) group, an oxy(aliphatic)hydroxyl group, an oxy(alkyl)hydroxyl group, an oxycarbonyl group, an oxysulfonyl group, a perfluoroalkyl group, a phosphate group, a saccharide group, a sulfamoyl group, a sulfonamido group, a sulfonylamino group, a sulfonyl group, a sulfoxide group, a thio group, a thioalkaryl group, a thioaralkyl group, a trifluoroalkyl group, and an ureido group, each of $R_1$ and $R_4$-$R_7$ is a pendant group independently selected from the group consisting of hydrogen, an acyl group, an acylamino group, an acyloxy group, an ethyl group, a propyl group, an isopropyl group, a butyl group, an isobutyl group, a t-butyl group, a pentyl group, a cyclopentyl group, an isopentyl group, a neopentyl group, a hexyl group, an isohexyl group, a cyclohexyl group, a 3-methylpentyl group, a 2,2-dimethylbutyl group, a 2,3-dimethylbutyl group, an alkenyl group, an alkynyl group, an alkoxy group, an amino group, an alkylamino group, an alkylarylamino group, a dialkylamino group, an alkylthio group, an alkarylthio group, a tolyl group, a naphthyl group, an arylamino group, a diarylamino group, an aryloxy group, an aralkyl group, an alkaryl group, an aralkoxy group, an alkaryloxy group, an arylthio group, an arylthio acyl group, an amino acid group, a carbamoyl group, a carbonamido group, a carboxyl group, a cyano group, a formyl group, a glycol group, a heteroalkyl group, a heteroaralkyl group, a heteroaryl group, a hydroxyl group, a nitro group, an oxy(aliphatic) group, an oxy(aliphatic)hydroxyl group, an oxy(alkyl)hydroxyl group, an oxycarbonyl group, an oxysulfonyl group, a perfluoroalkyl group, a phosphate group, a saccharide group, a sulfamoyl group, a sulfonamido group, a sulfonylamino group, a sulfonyl group, a sulfoxide group, a thio group, a thioalkaryl group, a thioaralkyl group, a trifluoroalkyl group, an ureido group, a substituted group thereof, a substituted methyl group, and a substituted phenyl group, and X is an anion independently selected from the group consisting of tetrafluoroborate, hexafluorophosphate, bis(oxalate)borate, hexafluoroarsenate, hexafluoroantimonate, tetrachloroaluminate, hydrogen sulfate, perchlorate, mesylate, chloride, bromide, iodide, an alkyl halide, a perhalogenated alkyl halide of a group VA element, trifluoromethanesulfonyl imide, trifluoromethanesulfonate, and trifluoroacetate.

6. An electrolyte solution comprising:
at least one solvent; and
an ionic phosphazene compound comprising a plurality of phosphorus-nitrogen units and at least one pendant group bonded to each phosphorus atom of the plurality of phosphorus-nitrogen units, the ionic phosphazene compound comprising:
a single, positively charged pendant group bonded to one of the phosphorus atoms of the plurality of phosphorus-nitrogen units through an oxygen atom and the positively charged pendant group comprises a trimethyl amino propanoxy group or a 4-pyridine propanoxy group; or
a positively charged phosphorus atom on one of the plurality of phosphorus-nitrogen units, the ionic phosphazene compound comprising the chemical structure

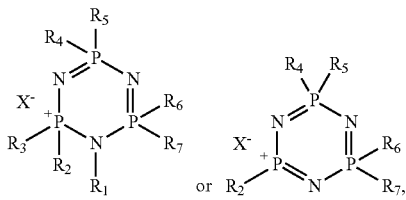

wherein each of $R_2$ and $R_3$ is a pendant group independently selected from the group consisting of an acyl group, an acylamino group, an acyloxy group, an alkenyl group, an alkynyl group, an alkoxy group, an amino group, an alkylamino group, an alkylarylamino group, a dialkylamino group, an alkylthio group, an alkarylthio group, an arylamino group, a diarylamino group, an aryloxy group, an aralkoxy group, an alkaryloxy group, an arylthio group, an arylthio acyl group, an amino acid group, a carbamoyl group, a carbonamido group, a carboxyl group, a cyano group, a formyl group, a glycol group, a heteroalkyl group, a heteroaralkyl group, a heteroaryl group, a hydroxyl group, a nitro group, an oxy (aliphatic) group, an oxy(aliphatic)hydroxyl group, an oxy(alkyl)hydroxyl group, an oxycarbonyl group, an oxysulfonyl group, a perfluoroalkyl group, a phosphate group, a saccharide group, a sulfamoyl group, a sulfonamido group, a sulfonylamino group, a sulfonyl group, a sulfoxide group, a thio group, a thioalkaryl group, a thioaralkyl group, a trifluoroalkyl group, and an ureido group, each of $R_1$ and $R_4$-$R_7$ is a pendant group independently selected from the group consisting of hydrogen, an acyl group, an acylamino group, an acyloxy group, an ethyl group, a propyl group, an isopropyl group, a butyl group, an isobutyl group, a t-butyl group, a pentyl group, a cyclopentyl group, an isopentyl group, a neopentyl group, a hexyl group, an isohexyl group, a cyclohexyl group, a 3-methylpentyl group, a 2,2-dimethylbutyl group, a 2,3-dimethylbutyl group, an alkenyl group, an alkynyl group, an alkoxy group, an amino group, an alkylamino group, an alkylarylamino group, a dialkylamino group, an alkylthio group, an alkarylthio group, a tolyl group, a naphthyl group, an arylamino group, a diarylamino group, an aryloxy group, an aralkyl group, an alkaryl group, an aralkoxy group, an alkaryloxy group, an arylthio group, an arylthio acyl group, an amino acid group, a carbamoyl group, a carbonamido group, a carboxyl group, a cyano group, a formyl group, a glycol group, a heteroalkyl group, a heteroaralkyl group, a heteroaryl group, a hydroxyl group, a nitro group, an oxy(aliphatic) group, an oxy(aliphatic)hydroxyl group, an oxy(alkyl)hydroxyl group, an oxycarbonyl group, an oxysulfonyl group, a perfluoroalkyl group, a phosphate group, a saccharide group, a sulfamoyl group, a sulfonamido group, a sulfonylamino group, a sulfonyl group, a sulfoxide group, a thio group, a thioalkaryl group, a thioaralkyl group, a trifluoroalkyl group, an ureido group, a substituted group thereof, a substituted methyl group, and a substituted phenyl group, and X is an anion independently selected from the group consisting of tetrafluoroborate, hexafluorophosphate, bis(oxalate)borate, hexafluoroarsenate, hexafluoroantimonate, tetrachloroaluminate, hydrogen sulfate, perchlorate, mesylate, chloride, bromide, iodide, an alkyl halide, a perhalogenated alkyl halide of a group VA element, trifluoromethanesulfonyl imide, trifluoromethanesulfonate, and trifluoroacetate.

7. The electrolyte solution of claim 6, wherein the electrolyte solution comprises from approximately 1% by weight to approximately 40% by weight of the ionic phosphazene compound.

8. The electrolyte solution of claim 6, wherein the electrolyte solution comprises from approximately 1% by weight to approximately 10% by weight of the ionic phosphazene compound.

9. The electrolyte solution of claim 6, wherein the electrolyte solution comprises from greater than approximately 40% to approximately 99% by weight of the ionic phosphazene compound.

10. The electrolyte solution of claim 6, wherein the at least one solvent comprises at least one of ethylene carbonate and ethyl methyl carbonate.

11. The electrolyte solution of claim 6, wherein the at least one solvent comprises at least one of an organic carbonate, an ester, an ether, and a siloxane.

12. The electrolyte solution of claim 6, wherein a viscosity of the ionic phosphazene compound is less than or equal to approximately 200 cP at 20° C.

13. The electrolyte solution of claim 6, further comprising at least one lithium salt.

14. An energy storage device, comprising:
a positive electrode, a negative electrode, a separator between the positive electrode and the negative electrode, and an electrolyte solution, the electrolyte solution comprising:
at least one solvent;
at least one lithium salt; and
an ionic phosphazene compound comprising a plurality of phosphorus-nitrogen units and at least one pendant group bonded to each phosphorus atom of the plurality of phosphorus-nitrogen units, the ionic phosphazene compound comprising:
a single, positively charged pendant group bonded to one of the phosphorus atoms of the plurality of phosphorus-nitrogen units through an oxygen atom and the positively charged pendant group comprises a trimethyl amino propanoxy group or a 4-pyridine propanoxy group; or a positively charged phosphorus atom on one of the plurality of phosphorus-nitrogen units, the ionic phosphazene compound comprising the chemical structure

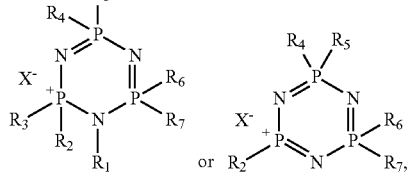

wherein each of $R_2$ and $R_3$ is a pendant group independently selected from the group consisting of an acyl group, an acylamino group, an acyloxy group, an alkenyl group, an alkynyl group, an alkoxy group, an amino group, an alkylamino group, an alkylarylamino group, a dialkylamino group, an alkylthio group, an alkarylthio group, an arylamino group, a diarylamino group, an aryloxy group, an aralkoxy group, an alkaryloxy group, an arylthio group, an arylthio acyl group, an amino acid group, a carbamoyl group, a carbonamido group, a carboxyl group, a cyano group, a formyl group, a glycol group, a heteroalkyl group, a heteroaralkyl group, a heteroaryl group, a hydroxyl group, a nitro group, an oxy(aliphatic) group, an oxy(aliphatic)hydroxyl group, an oxy(alkyl)hydroxyl group, an oxycarbonyl group, an oxysulfonyl group, a perfluoroalkyl group, a phosphate group, a saccharide group, a sulfamoyl group, a sulfonamido group, a sulfonylamino group, a sulfonyl group, a sulfoxide group, a thio group, a thioalkaryl group, a thioaralkyl group, a trifluoroalkyl group, and an ureido group, each of $R_1$ and $R_4$-$R_7$ is a pendant group independently selected from the group consisting of hydrogen, an acyl group, an acylamino group, an acyloxy group, an ethyl group, a propyl group, an isopropyl group, a butyl group, an isobutyl group, a t-butyl group, a pentyl group, a cyclopentyl group, an isopentyl group, a neopentyl group, a hexyl group, an isohexyl group, a cyclohexyl group, a 3-methylpentyl group, a 2,2-dimethylbutyl group, a 2,3-dimethylbutyl group, an alkenyl group, an alkynyl group, an alkoxy group, an amino group, an alkylamino group, an alkylarylamino group, a dialkylamino group, an alkylthio group, an alkarylthio group, a tolyl group, a naphthyl group, an arylamino group, a diarylamino group, an aryloxy group, an aralkyl group, an alkaryl group, an aralkoxy group, an alkaryloxy group, an arylthio group, an arylthio acyl group, an amino acid group, a carbamoyl group, a carbonamido group, a carboxyl group, a cyano group, a formyl group, a glycol group, a heteroalkyl group, a heteroaralkyl group, a heteroaryl group, a hydroxyl group, a nitro group, an oxy(aliphatic) group, an oxy(aliphatic)hydroxyl group, an oxy(alkyl)hydroxyl group, an oxycarbonyl group, an oxysulfonyl group, a perfluoroalkyl group, a phosphate group, a saccharide group, a sulfamoyl group, a sulfonamido group, a sulfonylamino group, a sulfonyl group, a sulfoxide group, a thio group, a thioalkaryl group, a thioaralkyl group, a trifluoroalkyl group, an ureido group, a substituted group thereof, a substituted methyl group, and a substituted phenyl group, and X is an anion independently selected from the group consisting of tetrafluoroborate, hexafluorophosphate, bis(oxalate)borate, hexafluoroarsenate, hexafluoroantimonate, tetrachloroaluminate, hydrogen sulfate, perchlorate, mesylate, chloride, bromide, iodide, an alkyl halide, a perhalogenated alkyl halide of a group VA element, trifluoromethanesulfonyl imide, trifluoromethanesulfonate, and trifluoroacetate.

15. The ionic liquid of claim 1, wherein a positive charge of the positively charged pendant group is located at a terminal portion of the positively charged pendant group.

16. An ionic liquid, comprising:
an ionic phosphazene compound comprising a plurality of phosphorus-nitrogen units and at least one pendant group bonded to each phosphorus atom of the plurality of phosphorus-nitrogen units, wherein a single pendant group of the at least one pendant group comprises a positively charged pendant group and the positively charged pendant group is bonded to the phosphorus atom through an oxygen atom, a sulfur atom, or a phosphorus atom, the ionic phosphazene compound further comprising a positively charged nitrogen atom or a positively charged phosphorus atom on one of the phosphorus-nitrogen units.

* * * * *